United States Patent
Egbertson et al.

[11] Patent Number: 5,981,584
[45] Date of Patent: Nov. 9, 1999

[54] FIBRINOGEN RECEPTOR ANTAGONIST PRODRUGS

[75] Inventors: Melissa S. Egbertson, Ambler; Steve D. Young; George D. Hartman, both of Lansdale; Jacquelynn J. Cook, Collegeville, all of Pa.

[73] Assignee: Merck & Co., Inc., Rahway, N.J.

[21] Appl. No.: 09/023,650

[22] Filed: Feb. 3, 1998

Related U.S. Application Data

[60] Provisional application No. 60/036,901, Feb. 6, 1997, abandoned.

[51] Int. Cl.[6] .................. A16K 31/24; C07C 307/02; C07C 309/06; C07C 317/06
[52] U.S. Cl. .................. 514/534; 514/536; 560/13
[58] Field of Search .................. 514/534, 536; 560/13

[56] References Cited

U.S. PATENT DOCUMENTS

| | | |
|---|---|---|
| 3,322,631 | 5/1967 | Sprague et al. . |
| 4,010,274 | 3/1977 | Giraldi et al. . |
| 4,122,255 | 10/1978 | Krapcho . |
| 4,243,807 | 1/1981 | Friebe et al. . |
| 4,313,947 | 2/1982 | Nakagawa et al. . |
| 4,622,331 | 11/1986 | Jozic . |
| 5,030,654 | 7/1991 | Barnish et al. . |
| 5,095,018 | 3/1992 | Kelley . |
| 5,166,154 | 11/1992 | Skiles et al. . |
| 5,227,490 | 7/1993 | Hartman et al. . |
| 5,260,316 | 11/1993 | Van Duzer et al. . |
| 5,264,420 | 11/1993 | Duggan et al. . |
| 5,272,158 | 12/1993 | Hartman et al. . |
| 5,278,161 | 1/1994 | Branca et al. . |
| 5,281,585 | 1/1994 | Duggan et al. . |
| 5,292,756 | 3/1994 | Duggan et al. . |
| 5,294,616 | 3/1994 | Duggan et al. . |
| 5,321,034 | 6/1994 | Duggan et al. . |

FOREIGN PATENT DOCUMENTS

| | | |
|---|---|---|
| 229 391 A1 | 7/1987 | European Pat. Off. . |
| 332 528 A1 | 9/1989 | European Pat. Off. . |
| 352 249 A1 | 1/1991 | European Pat. Off. . |
| 405 537 A1 | 1/1991 | European Pat. Off. . |
| 540 334 A1 | 5/1993 | European Pat. Off. . |
| 2612185 | 9/1988 | France . |

OTHER PUBLICATIONS

Guertin, et al., Amer. Chem. Soc., AN 127:136073, 1996 (Abstract).
Volkhard, et al., Amer. Chem. Soc., AN 128:180416, 1996 (Abstract).
Sugimoto et al., J. Med. Chem., "7–(Ethoxycarbonyl)–6, 8–dimethyl–2–phenyl–1(2H)–phthalazinone Derivatives: . . . ", vol. 27, pp. 1300–1305 (1984).

*Primary Examiner*—Johann Richter
*Assistant Examiner*—Taofiq A. Solola
*Attorney, Agent, or Firm*—Richard S. Parr; Melvin Winokur

[57] ABSTRACT

Fibrinogen receptor antagonist prodrugs having the structure, for example, of

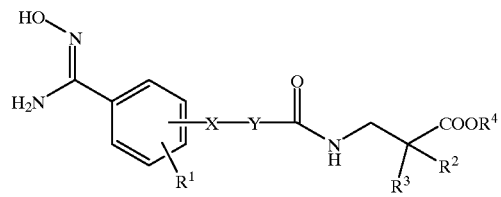

more particularly,

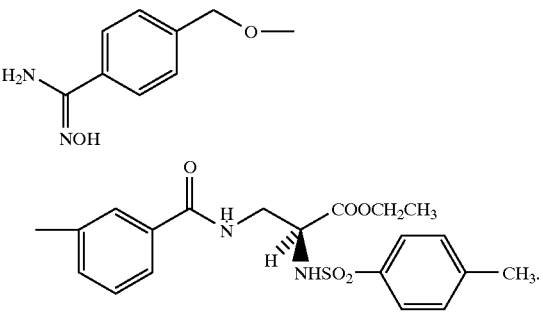

13 Claims, No Drawings

FIBRINOGEN RECEPTOR ANTAGONIST PRODRUGS

CROSS REFERENCE TO RELATED APPLICATIONS

This patent application claims benefit to provisional patent application U.S. Ser. No. 60/036,901, filed Feb. 6, 1997, now abandoned.

BACKGROUND OF THE INVENTION

The invention relates generally to inhibiting the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothelial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in *Science*, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci. U.S.A.*, 84, 6471–6475, (1987), describes an Arg-Gly-Asp directed adhesion receptor expressed by human endothelial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol. Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the stereochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In *Proc. Nat'l Acad. Sci. U.S.A.*, 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661,111 and U.S. Pat. No. 4,578,079.

Ruggeri et al., *Proc. Nat'l Acad. Sci. U.S.A.*, 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *Biochem.* 23, 1767–1774 (1984); Ginsberg et al., *J. Biol. Chem.* 260(7), 3931–3936 (1985); and Haverstick et al., *Blood* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., *J. Biol. Chem.*, 262, 16157–16163 (1987); Huang et al., Biochemistry, 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., *J. Biol. Chem.*, 263, 19827–19832 (1988). See also, Dennis et al., *Proc. Nat'l Acad. Sci. USA*, 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No. 5,023,233 discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. WO 9014103 describes the use of antibody-poly-peptide conjugates wherein said polypeptides contain the Arg-Gly-Asp (RGD) sequence.

WO 9111458 discloses the use of large cyclic peptides containing RGD flanked by proline residues which are platelet aggregation inhibitors. WO 9101331 discloses small cyclic platelet aggregation inhibitors which are synthetic cyclic pentapeptides containing the tripeptide sequence Arg-Gly-Asp and a thioether linkage in the cycle. U.S. Pat. No. 5,051,405 also discloses the use of peptides and pseudopeptides such as N-amidino-piperidine-3-carboxylglycyl-L-aspartyl-L-valine that inhibit platelet aggregation and thrombus formation in mammalian blood. EP 445 796 discloses linear compounds which can include internal piperazinyl or piperidinyl derivatives. EP437 367 discloses linear polypeptide fibrinogen receptor antagonists. U.S. Pat. No. 5,256,812 discloses compounds of the $R^1$—A—$(W)_a$—X—$(CH_2)_b$—$(Y)_c$—B—Z—COOR wherein $R^1$ is a guandidino or amidino moiety and A and B are chosen from specific monosubstituted aryl or heterocyclic moieties.

While a multitude of compounds or peptide analogs believed to inhibit platelet aggregation by inhibiting binding of a blood platelet to fibrinogen are known, the present invention provides novel fibrinogen receptor antagonist prodrugs of antagonists that have significant binding activity and are, therefore, useful for the reasons stated herein.

SUMMARY OF THE INVENTION

Fibrinogen receptor antagonist prodrugs having the structure, for example, of

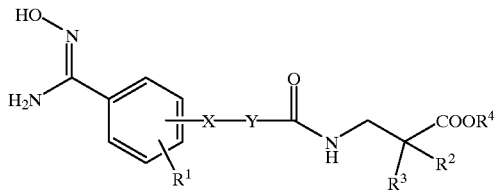

more particularly,

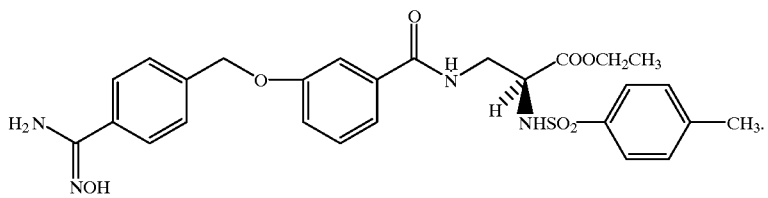

Compounds of the invention, or pharmaceutically acceptable salts thereof, are useful in the manufacture of a medicament for inhibiting the aggregation of blood platelets, inhibiting angiogenesis, inhibiting osteoclast mediated bone resorption, preventing platelet thrombosis, preventing thromboembolism or preventing reocclusion, in a mammal.

DETAILED DESCRIPTION OF THE INVENTION

The invention relates to compounds having the formula

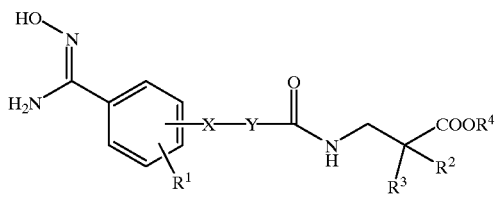

or a pharmaceutically acceptable salt, wherein

X is
$(CH_2)_q$,
$(CH_2)_m O(CH_2)_p$,
$(CH_2)_m NR^{11}(CH_2)_p$,
$(CH_2)_m C(O)NR^{11}(CH_2)_p$,
$(CH_2)_m NR^{11}C(O)(CH_2)_p$,
$(CH_2)_m C(O)(CH_2)_p$,
$(CH_2)_m C(S)(CH_2)_p$,
$(CH_2)_m SO_2(CH_2)_p$,
$(CH_2)_m S(CH_2)_p$,
$(CH_2)_m SO(CH_2)_p$,
$(CH_2)_m SO_2 NR^{11}(CH_2)_p$,
$(CH_2)_m C=C(CH_2)_p$, or
$(CH_2)_m CH(OH)(CH_2)_p$, where m and p are integers independently chosen from 0–6, q is an integer chosen from 1–6, and $R^{11}$ is selected from the group consisting of
hydrogen,
hydroxyl,
$C_{1-10}$ alkyl
$C_{3-8}$ cycloalkyl
aryl,
aryl $C_{1-8}$ alkyl-,
amino,
amino $C_{1-8}$ alkyl-,
$C_{1-3}$ acylamino-,
$C_{1-3}$ acylamino $C_{1-8}$ alkyl-,
$C_{1-6}$ alkylamino-,
$C_{1-6}$ alkylamino-, $C_{1-8}$ alkyl-,
$C_{1-6}$ dialkylamino-,
$C_{1-6}$ dialkylamino $C_{1-8}$ alkyl-,
$C_{1-4}$ alkoxy,
$C_{1-4}$ alkoxy $C_{1-6}$ alkyl-,
carboxy,
carboxy $C_{1-6}$ alkyl-,
$C_{1-3}$ alkoxycarbonyl-,
$C_{1-3}$ alkoxycarbonyl $C_{1-6}$ alkyl-,
carboxyoxy-,
carboxy $C_{1-6}$ alkyloxy-,
hydroxy $C_{1-6}$ alkyl-,
$C_{1-8}$ alkylcarbonyloxy $C_{1-4}$ alkyloxycarbonyl-, and
aryl $C_{1-8}$ alkylcarbonyloxy $C_{1-4}$ alkyloxycarbonyl-;

Y is

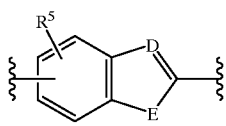

i)

where D and E are independently chosen from C, NH, $N(CH_3)$, $N(CH_2CH_3)$, $N(CHCH_2CH_2)$, O and S, and $R^5$ is independently selected from the group consisting of
hydrogen,
$C_{1-10}$ alkyl-,
aryl,
aryl $C_{1-8}$ alkyl-,
oxo,
thio,
amino,
amino $C_{1-8}$ alkyl-,
$C_{1-3}$ acylamino-,
$C_{1-3}$ acylamino $C_{1-8}$ alkyl-,
$C_{1-6}$ alkylamino-,
$C_{1-6}$ alkylamino $C_{1-8}$ alkyl-,
$C_{1-6}$ dialkylamino-,
$C_{1-6}$ dialkylamino $C_{1-8}$ alkyl-, $C_{1-4}$ alkoxy
$C_{1-4}$ alkoxy $C_{1-6}$ alkyl-,
carboxy,
carboxy $C_{1-6}$ alkyl-,
$C_{1-3}$ alkoxycarbonyl-,
$C_{1-3}$ alkoxycarbonyl $C_{1-6}$ alkyl-,
carboxyoxy-,
carboxy $C_{1-6}$ alkyloxy-,
hydroxy, and
hydroxy $C_{1-6}$ alkyl;

ii)

, iii)

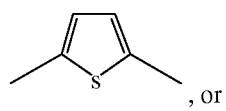
, or iv) AB, wherein A and B, which form a fused ring system sharing adjacent carbon and nitrogen atoms, are defined as follows:
A is a 5, 6 or 7 membered saturated, partially saturated, or unsaturated ring containing 1, 2 or 3 heteroatoms selected from O, S or N;
B is a 5, 6 or 7 membered saturated, partially saturated, or unsaturated ring containing 1, 2 or 3 heteroatoms selected from O, S or N;
$R^1$ is
hydrogen
$C_{1-6}$ alkyl
carboxy,
carboxy $C_{1-6}$ alkyl-,
$C_{1-6}$ alkylcarboxy -,
$C_{1-6}$ alkylcarboxy $C_{1-6}$ alkyl-,
oxo,
$C_{1-6}$ alkyloxy-,
oxo $C_{1-6}$ alkyl-,
$C_{1-6}$ alkyloxy $C_{1-6}$ alkyl-,
hydroxy,
hydroxy $C_{1-6}$ alkyl-,
aryl,
aryl $C_{1-6}$ alkyl-, or
halogen;
$R^2$ and $R^3$ are independently selected from the group consisting of
hydrogen,
fluoro,
hydroxy $C_{1-6}$ alkyl-,
carboxy,
carboxy $C_{1-6}$ alkyl-,
hydroxyl,
$C_{1-6}$ alkyloxy-,
aryl $C_{1-6}$ alkyloxy-,
$C_{3-8}$ cycloalkyl-,
$C_{1-8}$ alkyl-,
aryl,
aryl $C_{1-6}$ alkyl-,
$C_{1-6}$ alkylcarbonyloxy-,
amino,
$C_{1-6}$ alkylamino-,
amino $C_{1-6}$ alkyl-,
$C_{1-6}$ alkylamino $C_{1-6}$ alkyl-,
arylamino-,
aryl $C_{1-6}$ alkylamino-,
arylamino $C_{1-6}$ alkyl-,
aryl $C_{1-6}$ alkylamino $C_{1-6}$ alkyl-,
amino $C_{1-6}$ alkyl-,
$C_{1-6}$ dialkylamino-,
$C_{1-6}$ dialkylamino $C_{1-6}$ alkyl-,
aminocarbonyloxy-,
aminocarbonyloxy $C_{1-6}$ alkyl-,
$C_{1-6}$ alkylaminocarbonyloxy-,
$C_{1-6}$ alkylaminocarbonyloxy $C_{1-6}$ alkyl-,
aryl aminocarbonyloxy-,
aryl aminocarbonyloxy $C_{1-6}$ alkyl-,
aryl $C_{1-6}$ alkylaminocarbonyloxy-,
aryl $C_{1-6}$ alkylaminocarbonyloxy $C_{1-6}$ alkyl-,
$C_{1-8}$ alkylsulfonylamino-,
$C_{1-8}$ alkylsulfonylamino $C_{1-6}$ alkyl-,
aryl sulfonylamino-,
aryl sulfonylamino $C_{1-6}$ alkyl-,
aryl $C_{1-6}$ alkylsulfonylamino-,
aryl $C_{1-6}$ alkylsulfonylamino $C_{1-6}$ alkyl-,
$C_{1-8}$ alkyloxycarbonylamino-,
$C_{1-8}$ alkyloxycarbonylamino $C_{1-8}$ alkyl-,
aryloxycarbonylamino-,
aryloxycarbonylamino $C_{1-8}$ alkyl-,
aryl $C_{1-8}$ alkyloxycarbonylamino-,
aryl $C_{1-8}$ alkyloxycarbonylamino $C_{1-8}$ alky-,
$C_{1-8}$ alkylcarbonylamino-,
$C_{1-8}$ alkylcarbonylamino $C_{1-6}$ alkyl-,
arylcarbonylamino-,
arylcarbonylamino $C_{1-6}$ alkyl-,
aryl $C_{1-8}$ alkylcarbonylamino-,
aryl $C_{1-8}$ alkylcarbonylamino $C_{1-6}$ alky-,
aminocarbonylamino-,
aminocarbonylamino $C_{1-6}$ alky-,
$C_{1-8}$ alkylaminocarbonylamino-,
$C_{1-8}$ alkylaminocarbonylamino $C_{1-6}$ alky-,
arylaminocarbonylamino-,
arylaminocarbonylamino $C_{1-6}$ alkyl-,
aryl $C_{1-8}$ alkylaminocarbonylamino-,
aryl $C_{1-8}$ alkylaminocarbonylamino $C_{1-6}$ alkyl-,
aminosulfonylamino-,
aminosulfonylamino $C_{1-6}$ alkyl-,
$C_{1-8}$ alkylaminosulfonylamino-,
$C_{1-8}$ alkylaminosulfonylamino $C_{1-6}$ alkyl-,
arylaminosulfonylamino-,
arylaminosulfonylamino $C_{1-6}$ alkyl-,
aryl $C_{1-8}$ alkylaminosulfonylamino-,
aryl $C_{1-8}$ alkylaminosulfonylamino $C_{1-6}$ alkyl-,
$C_{1-6}$ alkylsulfonyl-,
$C_{1-6}$ alkylsulfonyl $C_{1-6}$ alkyl-,
aryl $C_{1-6}$ alkylsulfonyl-,
aryl $C_{1-6}$ alkylsulfonyl $C_{1-6}$ alkyl-,
$C_{1-6}$ alkylcarbonyl-,
$C_{1-6}$ alkylcarbonyl $C_{1-6}$ alkyl-,
aryl $C_{1-6}$ alkylcarbonyl-,
aryl $C_{1-6}$ alkylcarbonyl $C_{1-6}$ alkyl-,
aminocarbonyl-,
aminocarbonyl $C_{1-8}$ alkyl-,
$C_{1-8}$ alkylaminocarbonyl-,
$C_{1-8}$ alkylaminocarbonyl $C_{1-8}$ alkyl-,
arylaminocarbonyl-,
arylaminocarbonyl $C_{1-8}$ alkyl-,
aryl $C_{1-8}$ alkylaminocarbonyl-,
aryl $C_{1-8}$ alkylaminocarbonyl $C_{1-8}$ alkyl-, aminosulfonyl-,
aminosulfonyl $C_{1-8}$ alkyl-,
$C_{1-8}$ alkylaminosulfonyl-,
$C_{1-8}$ alkylaminosulfonyl $C_{1-8}$ alkyl-,
arylaminosulfonyl-,
arylaminosulfonyl $C_{1-8}$ alkyl-,
aryl $C_{1-8}$ alkylaminosulfonyl-,
aryl $C_{1-8}$ alkylaminosulfonyl $C_{1-8}$ alkyl-,
$C_{3-8}$ cycloalkylsulfonylamino-,
$C_{1-8}$ alkyloxyarylsulfonylamino-,
thiophenylsulfonylamino-, and

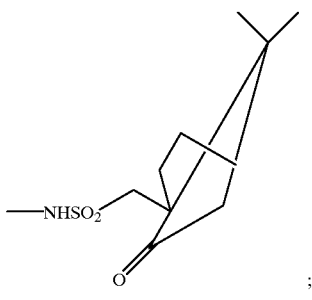
;

and
R$^4$ is
hydrogen,
$C_{1-8}$ alkyl-,
aryl,
aryl $C_{1-6}$ alkyl-,
$C_{1-8}$ alkylcarbonyloxy $C_{1-4}$ alkyl-, or
aryl $C_{1-8}$ alkylcarbonyloxy $C_{1-4}$ alkyl-.

One class of compounds of the invention has the formula

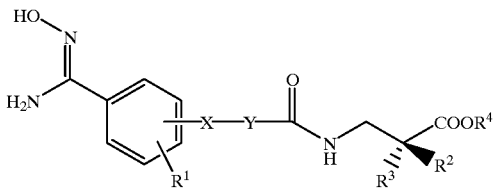

or a pharmaceutically acceptable salt, wherein
Y is i)

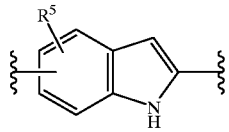

where R$^5$ is independently selected from the group consisting of
hydrogen,
$C_{1-10}$ alkyl-,
aryl,
aryl $C_{1-8}$ alkyl-,
oxo,
thio,
amino,
amino $C_{1-8}$ alkyl-,
$C_{1-3}$ acylamino-,
$C_{1-3}$ acylamino $C_{1-8}$ alkyl-,
$C_{1-6}$ alkylamino-, $C_{1-6}$ alkylamino-, $C_{1-8}$ alkyl-,
$C_{1-6}$ dialkylamino-,
$C_{1-6}$ dialkylamino $C_{1-8}$ alkyl-,
$C_{1-4}$ alkoxy-,
$C_{1-4}$ alkoxy $C_{1-6}$ alkyl-,
carboxy,
carboxy $C_{1-6}$ alkyl-,
$C_{1-3}$ alkoxycarbonyl-,
$C_{1-3}$ alkoxycarbonyl $C_{1-6}$ alkyl-,
carboxyoxy-,
carboxy $C_{1-6}$ alkyloxy-,
hydroxy, and
hydroxy $C_{1-6}$ alkyl-;

ii)

, iii)

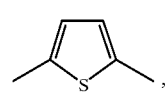, iv)
AB, where AB is selected from the group consisting of
a)

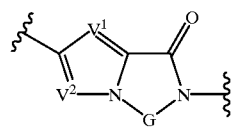

wherein V$^1$ and V$^2$ is N or CR$^6$ and G is CH$_2$, CH$_2$—CH$_2$, CH$_2$C(R$^7$)$_2$CH$_2$, or

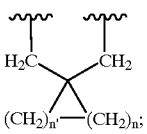

R$^6$ is H, branched or straight chain $C_{1-4}$ substituted or unsubstituted alkyl, branched or straight chain lower alkenyl, $C_{1-4}$ alkylaryl, substituted aryl, or 5 or 6 membered heteroaryl containing 1, 2, or 3 N, S, or O heteroatoms
wherein substituted alkyl is hydroxy-substituted or $C_{1-4}$ alkoxy-substituted alkyl, and wherein substituted aryl is substituted by one, two or three of the following groups:
halogen, $C_{1-4}$ alkoxy, hydroxy, or $C_{1-4}$ alkyl;
R$^7$ is H, branched or straight chain $C_{1-4}$ substituted or unsubstituted alkyl-, branched or straight chain lower alkenyl, $C_{1-4}$ alkylaryl, substituted aryl, or 5 or 6 membered heteroaryl containing 1, 2, or 3 N, S, or O heteroatoms
wherein substituted alkyl is hydroxy-substituted or $C_{1-4}$ alkoxy-substituted alkyl, and wherein substituted aryl is substituted by one, two or three of the following groups: halogen, $C_{1-4}$ alkoxy, hydroxy, or $C_{1-4}$ alkyl;

b)

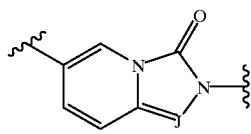

wherein J=N or CR⁸,
wherein R⁸=CN, C(O)N(R⁹)R¹⁰,

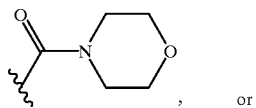, or

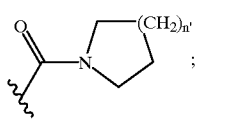;

R⁹ is is H, branched or straight chain $C_{1-4}$ substituted or unsubstituted alkyl, branched or straight chain lower alkenyl, $C_{1-4}$ alkylaryl, substituted aryl, or 5 or 6 membered heteroaryl containing 1, 2, or 3 N, S, or O heteroatoms
  wherein substituted alkyl is hydroxy-substituted or $C_{1-4}$ alkoxy-substituted alkyl, and wherein substituted aryl is substituted by one, two or three of the following groups: halogen, $C_{1-4}$ alkoxy, hydroxy, or $C_{1-4}$ alkyl;

R¹⁰ is H, branched or straight chain $C_{1-4}$ alkyl;
wherein n and n' are 0–7;

c)

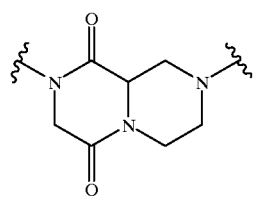;

d)

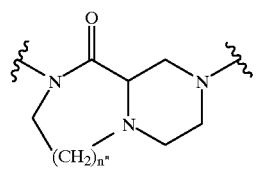;

e)

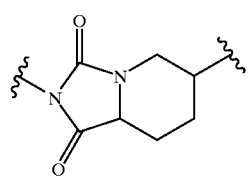; or f)

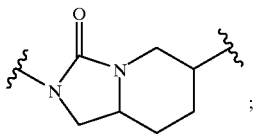;

wherein n" is 0–3.

In a group of the class, the compounds have the formula

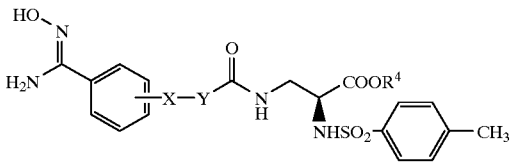

or a pharmaceutically acceptable salt, wherein wherein

X is —CH₂—, —O—, —CH₂—O—, or —NH—C(O)—;
R⁴ is —CH₂CH₃ or —C(CH₃)₃.

In a subgroup of the group, the compounds have the formula

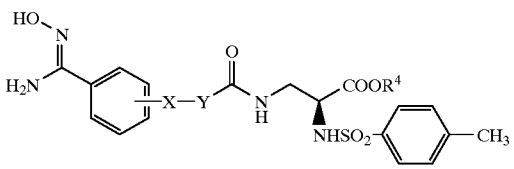

or a pharmaceutically acceptable salt, wherein

Y is

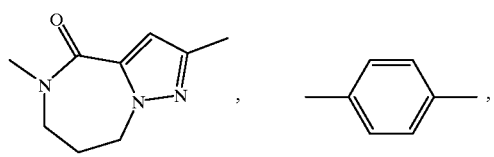

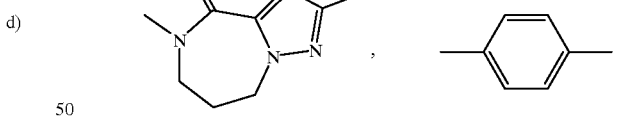

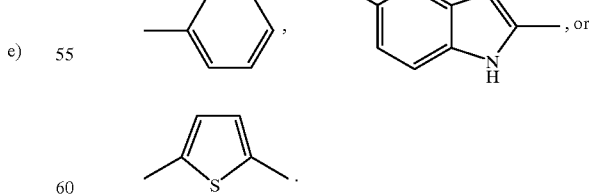

Specific exemplifications of this group are shown below:

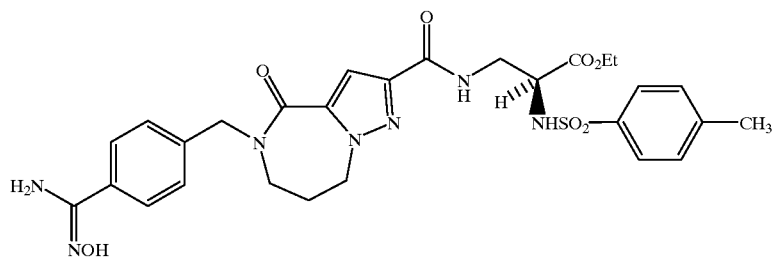
1-5
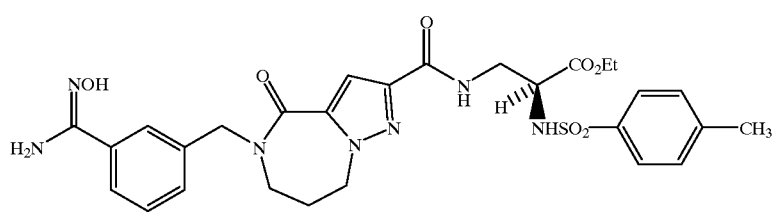
2-3
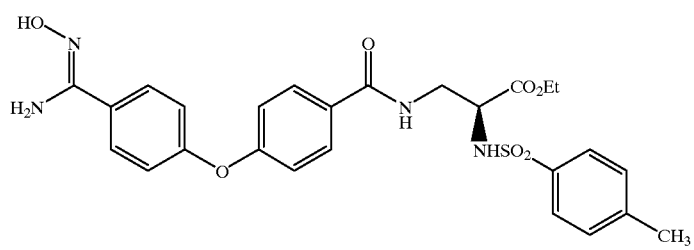
3-4
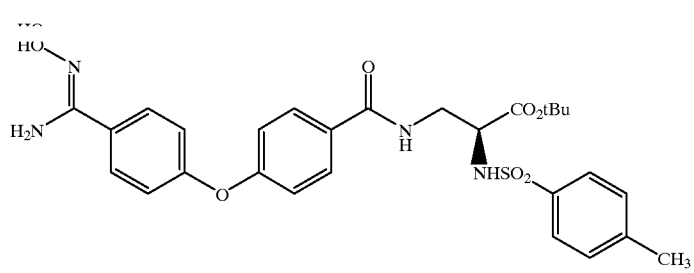
3-7
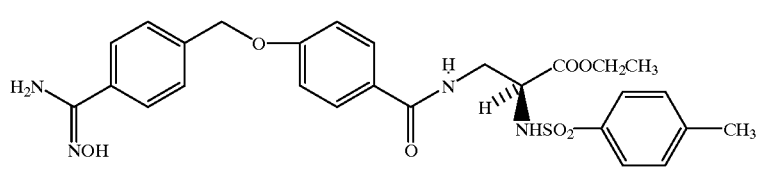
4-6
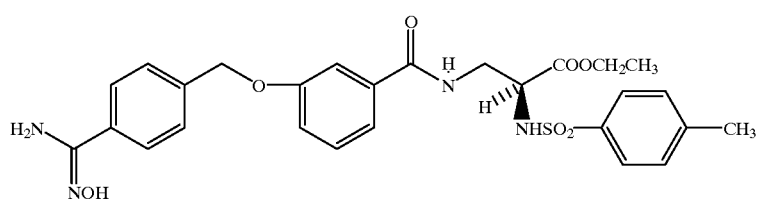
5-5
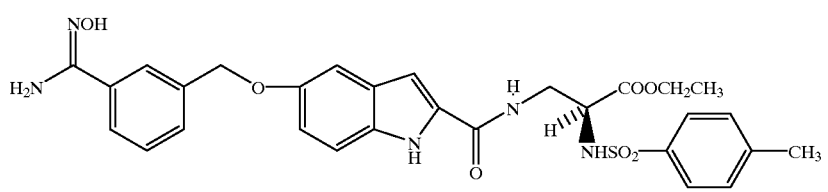
6-6

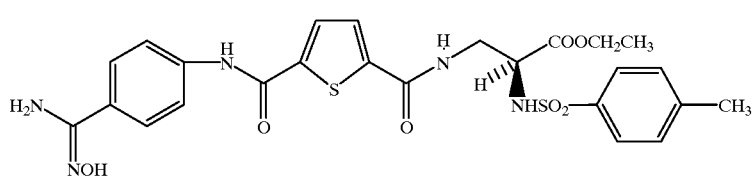

7-5 and pharmaceutically acceptable salts.

The prodrugs may be administered in low amounts relative to the amounts of antagonist that would ordinarily be administered. The prodrugs may be administered orally. The prodrugs retain structural integrity while passing though the gastrointestinal system, and are effectively delivered to cells. They are subjected to metabolic reactions to form the active acid which then interacts with the platelet receptor site.

A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

One test which is used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet-aggregation assay used to determine inhibition associated with the acids of the compounds claimed in the instant invention, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets ($2\times10^8$ per ml), fibrinogen (100 micrograms per ml (ug/ml)), $Ca^{2+}$(1 mM), and the compound to be tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

The active amidine-acids of these compounds have been evaluated in vitro and found to have an $IC_{50}$ for inhibiting platelet aggregation of between about 1.0 nM and 10,000 nM.

Additionally, these compounds are useful for treating mammals suffering from a bone condition caused or mediated by increased bone resorption, who are in need of such therapy. Pharmacologically effective amounts of the compounds, including pharamaceutically acceptable salts thereof, are administered to the mammal, to inhibit the activity of mammalian osteoclasts.

Additionally, these compounds are useful for treating angiogenesis (formation of new blood vessels). It has been postulated that the growth of tumors depends on an adequate blood supply, which in turn is dependent on the growth of new vessels into the tumor. Inhibition of angiogenesis can cause tumor regression in animal models. (See, *Harrison's Principles of Internal Medicine*, 12th ed., 1991). These compounds are therefore useful in the treatment of cancer for inhibiting tumor growth. (See e.g., Brooks et al., *Cell*, 79:1157–1164 (1994)).

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Compounds of the present invention may be chiral; included within the scope of the present invention are racemic mixtures and separated enantiomers of the general formula. Furthermore, all diastereomers, including E, Z isomers, of the general formula are included in the present scope. Furthermore, hydrates as well as anhydrous compositions and polymorphs of the general formula are within the present invention.

The term "pharmaceutically effective amount" shall mean that amount of a drug or pharmaceutical agent that will elicit the biological or medical response of a tissue, system or animal that is being sought by a researcher or clinician. The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like, straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like, or straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "aryl" means a 5- or 6-membered aromatic ring containing 0, 1, or 2 heteroatoms selected from O, N, and S, e.g. phenyl, pyridine, pyrimidine, imidazole, thiophene, oxazole, isoxazole, thiazole, and amino- and halogen- substituted derivatives thereof.

The terms "alkyloxy" or "alkoxy" include an alkyl portion where alkyl is as defined above, e.g., methyloxy, propyloxy, and butyloxy.

The terms "arylalkyl" and "alkylaryl" include an alkyl portion where alkyl is as defined above and to include an aryl portion where aryl is as defined above. The $C_{0-n}$ or $C_{1-n}$ designation where n may be an integer from 1–10 or 2–10 respectively refers to the alkyl component of the arylalkyl or alkylaryl unit. Examples of arylalkyl include benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include toluene, ethylbenzene, propylbenzene, methylpyridine, ethylpyridine, propylpyridine, butylpyridine, butenylpyridine, and pentenylpyridine.

The term "halogen" includes fluorine, chlorine, iodine and bromine.

The term "oxy" means an oxygen (O) atom. The term "thio" means a sulfur (S) atom. Under standard nonmenclature used throughout this disclosure, the terminal portion of the designated side chain is described first followed by the adjacent functionality toward the point of attachment. For example, a methylene substituted with ethylcarbonylamino is equivalent to

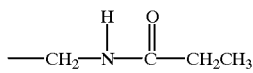

In the schemes and examples below, various reagent symbols have the following meanings:
BOC
  (or Boc): t-butyloxycarbonyl
  Pd-C: Palladium on activated carbon catalyst
  DMF: Dimethylformamide
  DMSO: Dimethylsulfoxide
  CBZ: Carbobenzyloxy
  $CH_2Cl_2$: Methylene chloride
  $CHCl_3$: chloroform
  EtOH: ethanol
  MeOH: methanol
  EtOAc: ethyl acetate
  HOAc: acetic acid
  BOP: Benzotriazol-1-yloxytris(dimethylamino) phosphonium, hexafluorophosphate
  EDC: 1-(3-Dimethylaminopropyl)-3-ethylcarbodiimide hydrochloride
  Oxone: potassium peroxymonosulfate
  LDA: Lithium diisopropylamide
  PYCLU: Chloro-N,N,N',N'-bis(pentamethylene) formamidinium hexafluorophosphate The compounds of the present invention can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention, or pharmaceutically acceptable salts thereof, are useful in the manufacture of a medicament for inhibiting binding of fibrinogen to the platelet membrane glycoprotein complex IIb/IIIa receptor, preventing platelet thrombosis, thromboembolism and reocclusion during and after thrombolytic therapy or after angioplasty or coronary artery bypass procedures, and preventing myocardial infarction in a mammal.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–100 mg/kg/day and most preferably 0.01–20 mg/kg/day. For example, a typical 90 kg patient would receive oral dosages ranging between about 0.9 mg/day and about 9 g/day, most preferably between about 0.9 mg/day and 1.8 g/day. Suitable pharmaceutical oral compositions such as tablets or capsules may contain, for example, 10 mg, 100 mg, 200 mg and 500 mg. Intravenously, the most preferred doses will range from about 1 to about 10 mg/kg/minute during a constant rate infusion.

Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the compounds herein described in detail are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the compound can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral prodrug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like.

Disintegrators include, without limitation, starch methyl cellulose, agar, bentonite, xanthan gum and the like.

Active drug can also be co-administered with the usual doses of suitable anticoagulation agents, such as heparin or warfarin (typically given in tablet doses between 1 and 20 mg daily during administration of the active drug), or thrombolytic agents such as tissue plasminogen activator (typically given in i.v. doses of between 20 and 150 mg over two hour period prior to or during administration of the active drug), to achieve beneficial effects in the treatment of various vascular pathologies. Such co-administration also includes administration if the active drug with doses of anticoagulant agents or thrombolyric agents less than the usual doses of those agents.

Compounds of the invention may prepared according to a number of methods familiar to persons skilled in the art.

EXAMPLE 1

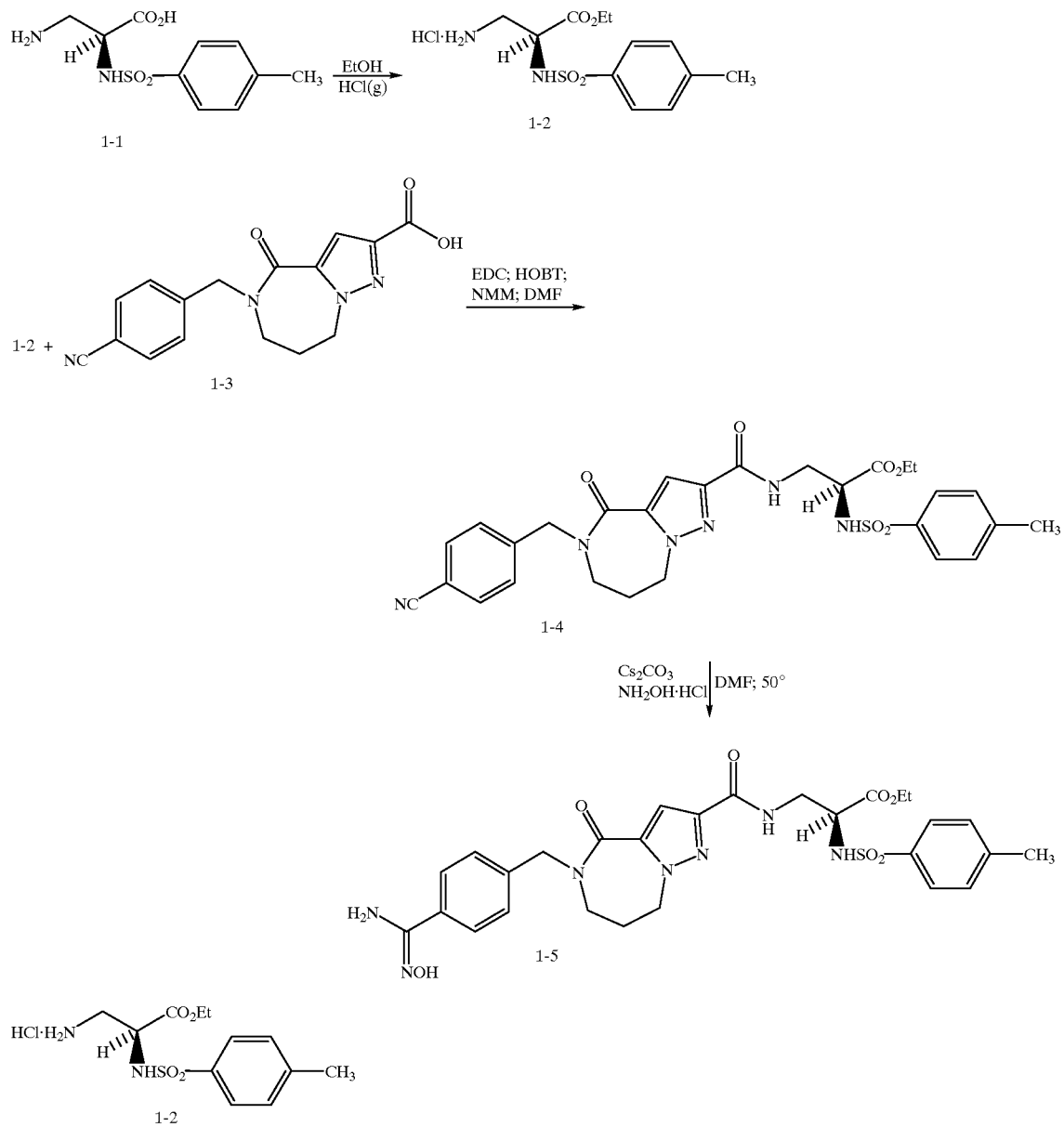

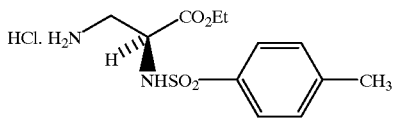

(R) 3-Amino-2-(toluene-4-sulfonylamino)propionic acid ethyl ester, hydrochloride 1-2

3-Amino-2-(toluene-4-sulfonylmethyl)propionic acid (1-1; 6.0 g; 23.2 mmol) was slurried in absolute EtOH and cooled to −15°. HCl (g) was bubbled through until the solution is saturated. The resulting homogeneous reaction mixture was stirred at −15° for 15 minutes, then at room temperature for 16 hrs. The reaction mixture was concentrated and placed under high vacuum to give 1-2 as a white fluffy solid.

$^1$H NMR (400 MHz, CDCl$_3$) d 8.32 (bs, 2H); 7.85–7.83 (d, 2H); 7.52 (d, 1H); 7.25 (s, 2H); 4.50 (bt, 1H); 3.93–3.90 (q, 2H); 3.62 (bs, 2H); 2.38 (s, 3H); 1.01–0.973 (t, 3H).

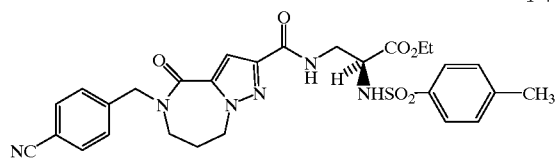

(R)-3-{[5-(4-cyanobenzyl)-4-oxo-5,6,7,8-tetrahydro-4H-1,5,8a-triazaazulene-2-carbonyl]-amino}-2-(toluene-4-sulfonylamino)propionic acid ethyl ester 1-4

5-(4-Cyano-benzyl)-4-oxo-5,6,7,8-tetrahydro-4H-1,5,8a-triazaazulene-2-carboxylic acid, 1-3 (synthesis is described in WO 94/18981) (1.0 g; 3.23 mmol) and 1-1 are dissolved in DMF. HOBT (3.55 mmol; 543 mg), NEt$_3$ (6.78 mmol; 0.40 mL), and EDC (3.55 mmol; 680 mg.) was added and the reaction mixture was stirred at RT overnight. The reaction mixture was diluted with EtOAc and H$_2$O, the layers were separated, and the organic layer was washed with 10% KHSO$_4$, Sat. NaHCO$_3$, and brine, dried (MgSO$_4$), filtered and concentrated. This material was purified by flash chromatography, the product was eluted with EtOAc to give 1-4 as a white solid.

$^1$H NMR(400 MHz, CDCl$_3$) d 7.73–7.67 (dd, 4H); 7.48–7.46 (d; 2H); 7.29–7.26 (m, 4H); 7.19 (bt, 1H); 5.61–5.59 (d, 1H); 4.80 (s, 2H); 4.43–4.41 (t, 2H); 4.04–4.02 (d, 3H); 3.83 (m, 1H); 3.76 (m, 1H); 3.37 (bs, 2H); 2.41 (s, 3H); 2.17 (bt, 2H); 1.26 (t, 3H).

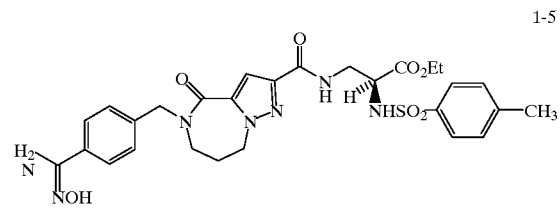

(R)-3-({5-[4-(N-hydroxycarbamimidoyl)benzyl]-4-oxo-5,6,7,8-tetrahydro-4H-1,5,8a-triazaazulene-2-carbonyl}amino)-2-(toluene-4-sulfonylamino)propionic acid ethyl ester 1-5

1-4 (1.3 g, 2.1 mmol) was dissolved in DMF. Cs$_2$CO$_3$ (9.66 mmol; 3.1 g) and NH$_2$OH (8 mmol; 543 mg.) was added and the heterogenous reaction mixture was stirred for 2 hours at 50°. H$_2$NOH (543 mg) was added and the reaction mixture was stirred at 50° for an additional 16 hours. The reaction mixture was filtered and the solids were washed with DMF. The filtrate was concentrated and the resulting solid is dissolved in 50/50 MeOH/EtOAc and loaded on a silica gel column. The product is eluted with 5% MeOH/EtOAc to give 1-5 as a white solid.

$^1$H NMR 400 MHz, (DMSO-d$_6$) d 9.60 (s, 1H); 8.25–8.22 (m, 2H); 7.66–7.64 (d, 2H); 7.61–7.59 (d, 2H) 7.37–7.35 (d, 2H); 7.28–7.26 (d, 2H); 6.95 (s, 1H); 4.69 (s, 2H); 4.41–4.38 (t, 2H); 4.02–4.00 (m, 1H); 3.86–3.82 (q, 2H); 3.48–3.47 (m, 1H); 3.34–3.32 (m, 2H); 2.88 (s, 3H); 2.06–2.03 (m, 2H); 1.00–0.97 (t, 3H).

EXAMPLE 2

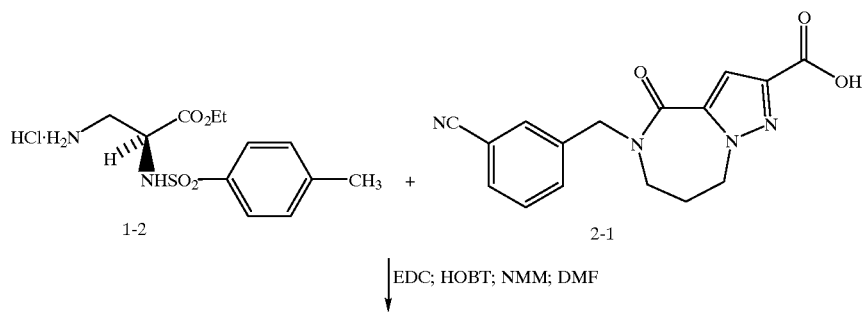

-continued

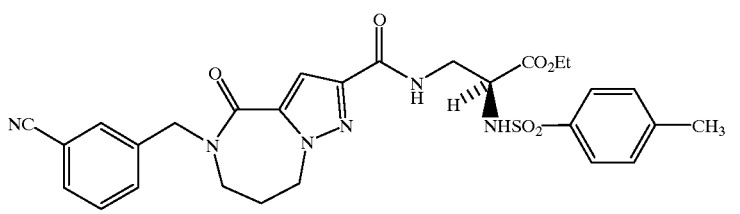
2-2

Cs₂CO₃
NH₂OH·HCl | DMF; 50°

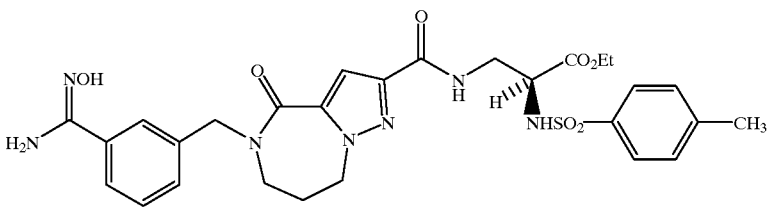
2-3

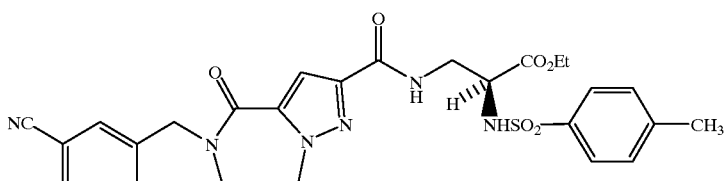
2-2

(R)-3-({5-[3-(N-hydroxycarbamimidoyl)benzyl]-4-oxo-5,6,7,8-tetrahydro-4H-1,5,8a-triazaazulene-2-carbonyl}amino)-2-(toluene-4-sulfonylamino) propionic acid ethyl ester 2-2

2-2 was prepared in a manner substantially the same as for 1-4. The synthesis for 5-(3-Cyano-benzyl)-4-oxo-5,6,7,8-tetrahydro-4H-1,5,8a-triaza-azulene-2-carboxylic acid (2-1) is disclosed in WO 94/18981.

$^1$H NMR (400 MHz CDCl₃) d 7.74–7.72 (d, 2H); 7.64–7.62 (m, 3H); 7.52–7.50 (t, 1H) 7.30 (s, 2H); 7.26 (s, 1H); 7.16(t, 1H); 5.56–5.55 (d, 2H); 4.77 (s, 2H); 4.43–4.41 (t, 2H); 4.13–4.00 (m, 3H) 3.9–3.82 (m, 1H); 3.78–3.70 (m, 1H); 3.37 (t, 2H); (2.41 s, 3H); 2.18–2.14 (m, 2H); 1.14–1.12 (t, 3H).

(R)-({5-[3-(N-hydroxycarbamimidoyl)benzyl]-4-oxo-5,6,7,8-tetrahydro-4H1,5,8a-triazaazulene-2-carbonyl}amino)-2-(toluene-4-sulfonylamino) propionic acid ethyl ester 2-3

2-3 was prepared in a manner substantially similar to example 1-5.

$^1$H NMR (400 MHz, DMSO-d₆) d 9.61 (s, 1H); 8.24–8.23 (t, 2H); 7.68 (s, 1H); 7.62–7.60 (d, 3H); 7.36–7.37 (m, 2H); 7.28–7.26 (d, 2H); 6.96 (s, 1H); 5.80 (s, 2H); 4.70 (s, 2H); 4.39 (t, 2H); 4.0 (m 1H); 3.84–3.82 (q, 2H); 3.49 (m, 1H); 3.33 (m 3H); 2.311 (s, 3H); 2.02 (m 2H); (0.99–0.96 (t, 3H).

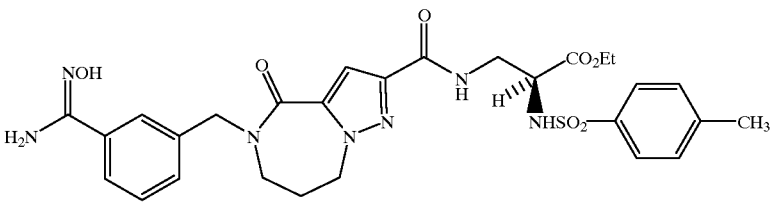
2-3

EXAMPLE 3
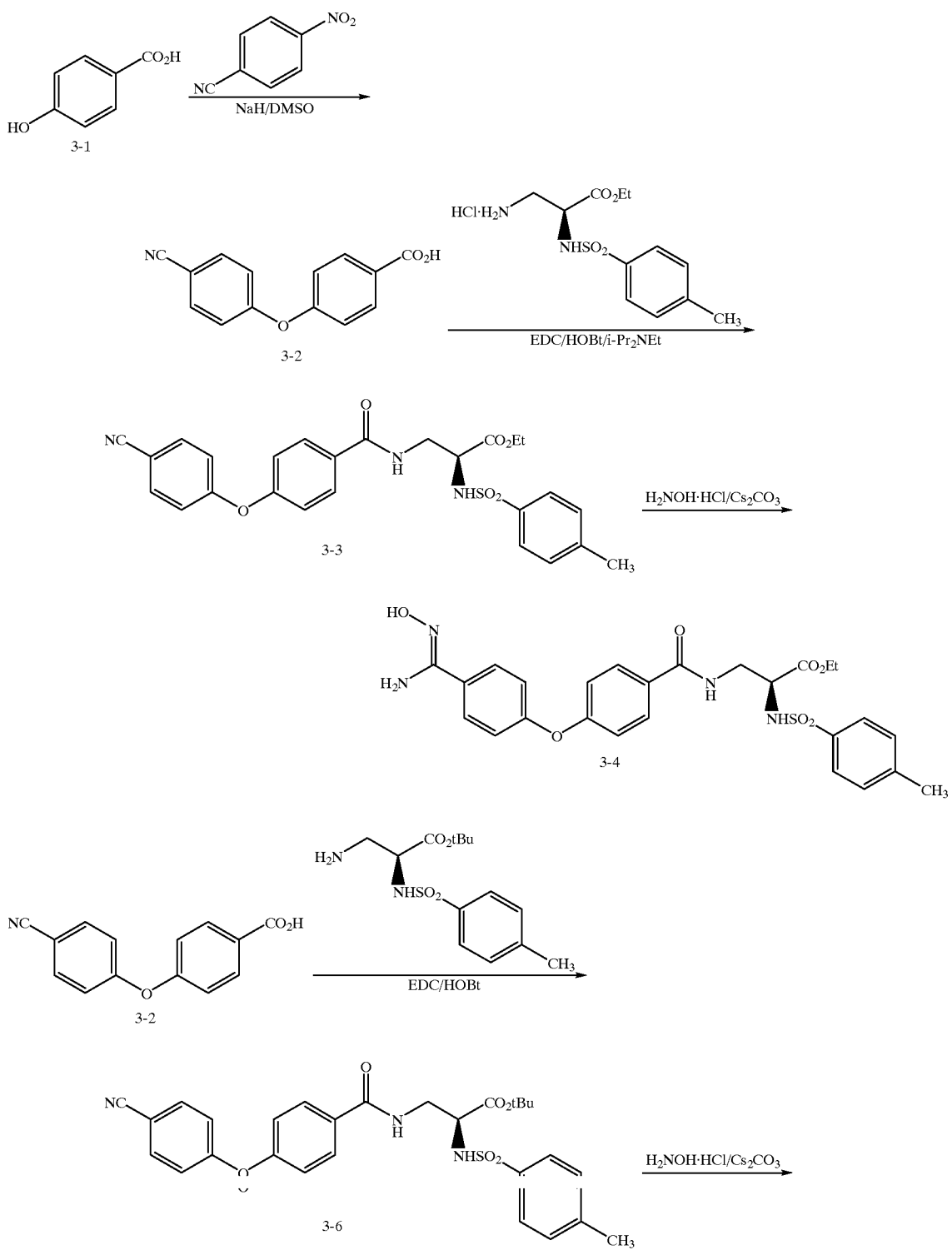

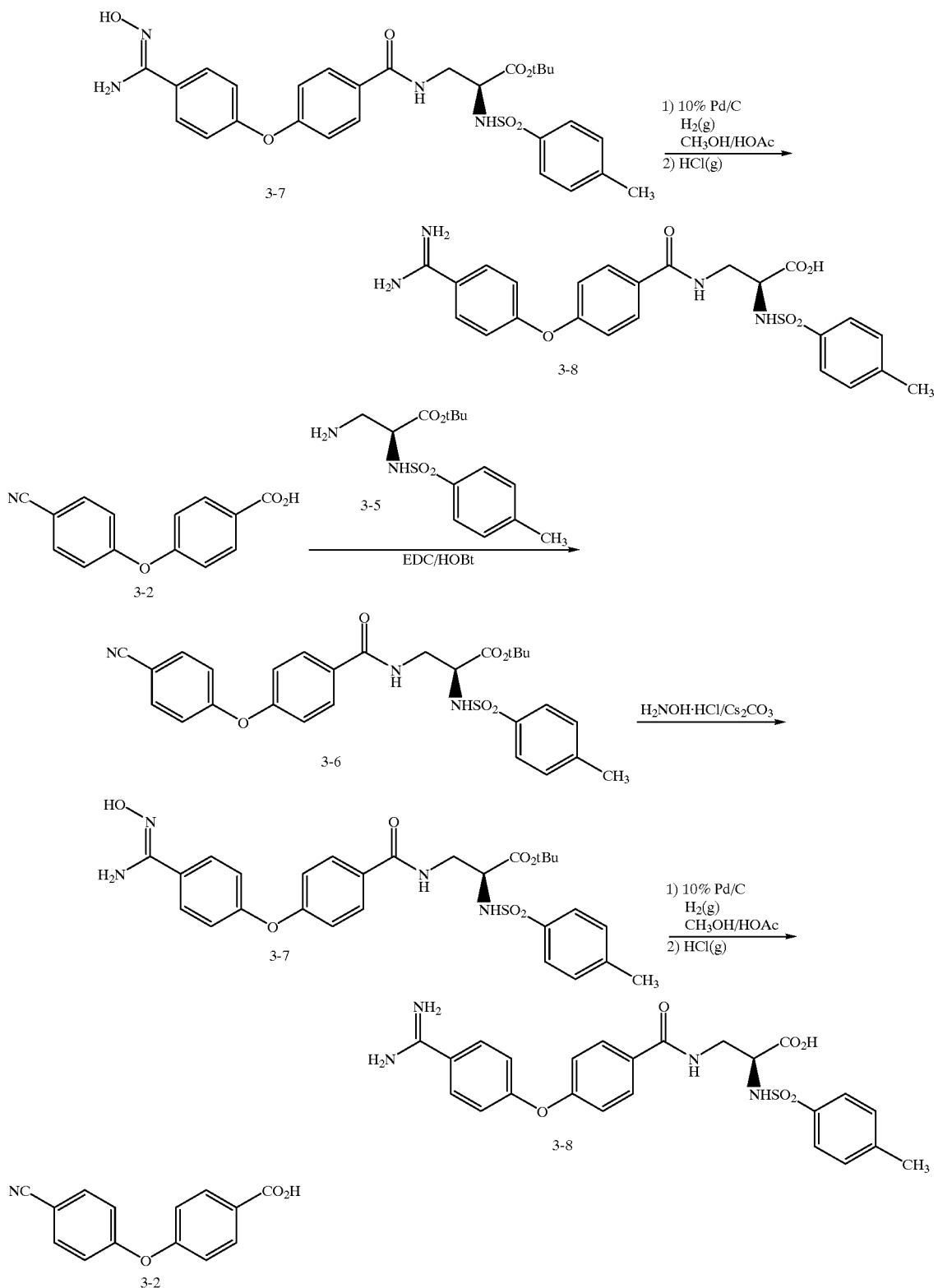
4-(4-Cyanophenoxy)benzoic acid 3-2
NaH (5.97 g, 149 mmol) was suspended in 100 mL DMSO under argon atmosphere and stirred for 30 min at rt. 4-Hydroxybenzoic acid (3-1, 10.0 g, 72.4 mmol) was added portionwise, and the mixture was stirred for 30 min at rt and 1 h at 80° C. 4-Nitrobenzonitrile (10.7 g, 72.2 mmol) was added, and the mixture stirred at 80° C. over 15 h. The resulting viscous suspension was diluted with $H_2O$ (50 mL)

and acidified with conc. HCl to pH 2. The resulting yellow precipitate was collected by vacuum filtration, recrystallized from EtOH, and washed with hexane to afford 3-2 as an orange solid. NMR (400 MHz, CDCl$_3$): d 8.15 (d, J=8 Hz, 2H), 7.67 (d, J=8 Hz, 2H), 7.20 (m, 4H).

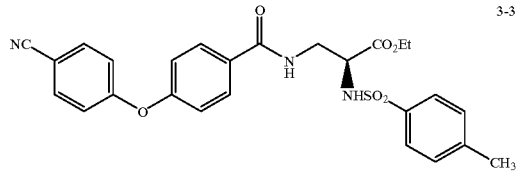

3-3

(R)-3-[4-(4-Cyanophenoxy)benzoylamino]-2-(toluene-4-sulfonyl-amino)-propionic acid ethyl ester 3-3

To a solution of 3-2 (0.73 g, 3.0 mmol) and amine 1-2 (1.00 g, 3.1 mmol) in 15 mL DMF was added diisopropylethylamine (0.50 mL, 2.9 mmol) followed by EDC (0.59 g, 3.1 mmol). The resultant mixture was stirred at rt over 36 h, then diluted with EtOAc, washed with H$_2$O, 10% aq. KHSO$_4$, sat'd NaHCO$_3$, and brine, dried (Na$_2$SO$_4$), filtered and concentrated in vacuo. The residue was purified by chromatography on SiO$_2$ eluting with 60% EtOAc/ hexane to afford 3-3 as a white solid. $R_f$ (60% EtOAc/hexane): 0.38. NMR (400 MHz, CDCl$_3$): d 7.86 (d, J=8 Hz, 2H), 7.72 (d, J=8 Hz, 2H), 7.64 (d, J=8 Hz, 2H), 7.30 (d, J=8 Hz, 2H), 7.10 (m, 4H), 6.76 (m, 1H), 5.59 (m, 1H), 4.0 (m, 4H), 3.61 (m, 1H), 2.42 (s, 3H), 1.16 (t, J=7 Hz, 3H).

MHz, d-6 DMSO): d 9.59 (s, 1H), 8.43 (m, 1H), 8.27 (s, 1H), 7.77 (d, J=9 Hz, 2H), 7.72 (d, J=9 Hz, 2H), 7.62 (d, J=8 Hz, 2H), 7.29 (d, J=8 Hz, 2H), 7.05 (m, 4H), 5.80 (s, 2H), 4.06 (m, 1H), 3.82 (q, J=7 Hz, 2H), 3.49 (m, 1H), 3.35 (m, 1H), 2.32 (s, 3H), 0.97 (t, J=7 Hz, 3H).

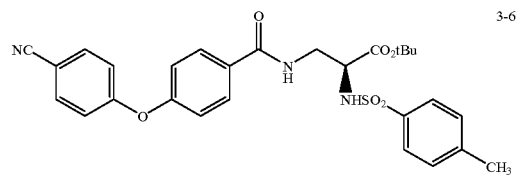

3-6

(R)-3-[4-(4-Cyanophenoxy)benzoylamino]-2-(toluene-4-sulfonylamino)-propionic acid tert-butyl ester 3-6

A solution of 3-2 (0.57 g, 2.4 mmol), 3-5 (0.75 g, 2.4 mmol), and EDC (0.47 g, 2.4 mmol) in 10 mL DMF was stirred at rt over 15 h. The mixture was then diluted with EtOAc, washed with H$_2$O, 10% aq. KHSO$_4$, sat'd NaHCO$_3$ and brine, dried (Na$_2$SO$_4$), filtered, and concentrated in vacuo. The residue was purified by chromatography, on SiO$_2$ eluting with 60% EtOAc/hexane to afford 3-6 as a white solid. $R_f$ (60% EtOAc/hexane): 0.52. NMR (400 MHz, CDCl$_3$): d 7.87 (d, J=9 Hz, 2H), 7.73 (d, J=8 Hz, 2H), 7.65 (d, J=9 Hz, 2H), 7.30 (d, J=8 Hz, 2H) 7.08 (m, 4H), 6.75 (m, 1H), 5.54 (m, 1H), 3.98 (m, 1H), 3.89 (m, 1H), 3.54 (m, 1H), 2.41 (s, 3H), 1.31 (s, 9H).

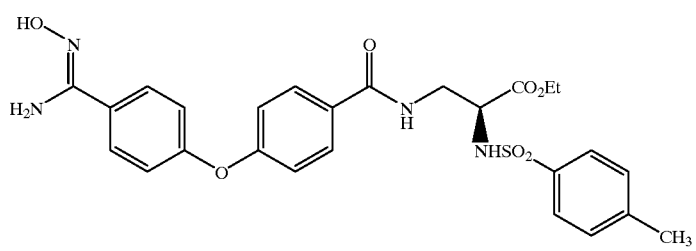

3-4

3-{4-[4-(Amino-hydroxyiminomethyl)phenoxy]benzoylamino}-2-(toluene-4-sulfonylamino)propionic acid ethyl ester 3-4

Example 3-4 was prepared in a manner substantially the same as for example 1-5. $R_f$ (EtOAc): 0.56. NMR (400

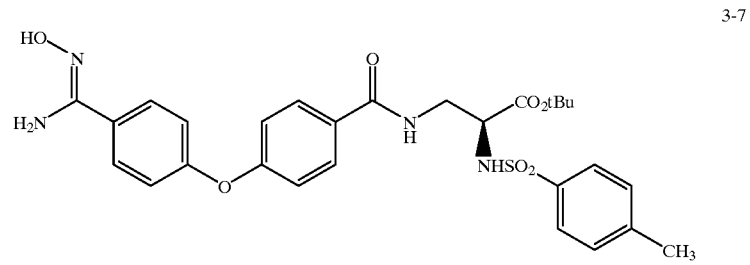

3-7

3-{4-[4-(Aminohydroxyiminomethyl)phenoxy]benzoylamino}-2-(toluene-4-sulfonylamino)propionic acid tert-butyl ester 3-7

Example 3-7 was prepared in a manner substantially the same as for example 1-5.

$R_f$ (80% EtOAc/hexane): 0.40. NMR (400 MHz, d-6 DMSO): d 9.59 (s, 1H), 8.40 (m, 1H), 8.18 (m, 1H), 7.79 (d, J=9 Hz, 2H), 7.72 (d, J=9 Hz, 2H), 7.63 (d, J=8 Hz, 2H), 7.30 (d, J=8 Hz, 2H), 7.05 (m, 4H), 5.80 (s, 2H) 4.00 (m, 1H), 3.48 (m, 1H), 3.36 (m, 1H), 2.32 (s, 3H), 1.16 (s, 9H).

(R)-3-{4-[4-(Aminoiminomethyl)phenoxy]benzoylamino}-2-(toluene-4-sulfonylamino)propionic acid 3-8

To a suspension of 3-7 (0.618 g, 1.09 mmol) in 5 mL $CH_3OH$ and 5 drops HOAc was added 0.19 g (31% by weight) of 10% Pd/C, and the resulting mixture was stirred under $H_2$ atmosphere at balloon pressure for 5 h. An additional 2 mL $CH_3OH$ and 0.5 mL HOAc were added, and the mixture stirred under $H_2$ atmosphere over 15 h. An additional portion of 10% Pd/C (0.20 g, 32% by weight) was then added and the mixture stirred for 15 h. The reaction was filtered through a pad of Celite, eluting with $CH_3OH$, and concentrated in vacuo. The residue was azeotroped with $CH_2Cl_2$, concentrated, and suspended in 15 mL EtOAc and cooled to −78° C. The mixture was treated with HCl (g) for 2.5 min, then allowed to warm to 0° C. and stir for 1 h. Concentration, azeotroping with $CH_2Cl_2$, and pumping at high vacuum afforded 3-8 as a white solid. NMR (400 MHz, $D_2O$+NaOD): d 7.67 (d, J=9 Hz, 2H), 7.47 (m, 4H), 7.10 (d, J=9 Hz, 2H), 7.02 (d, J=9 Hz, 2H), 6.95 (d, J=8 Hz, 2H), 3.57 (m, 2H), 3.09 (dd, J=9.5, 13 Hz), 2.07 (s, 3H).

3-8

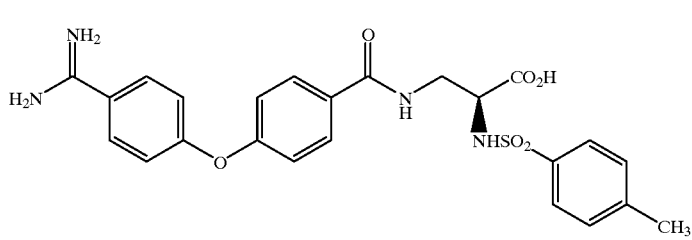

EXAMPLE 4

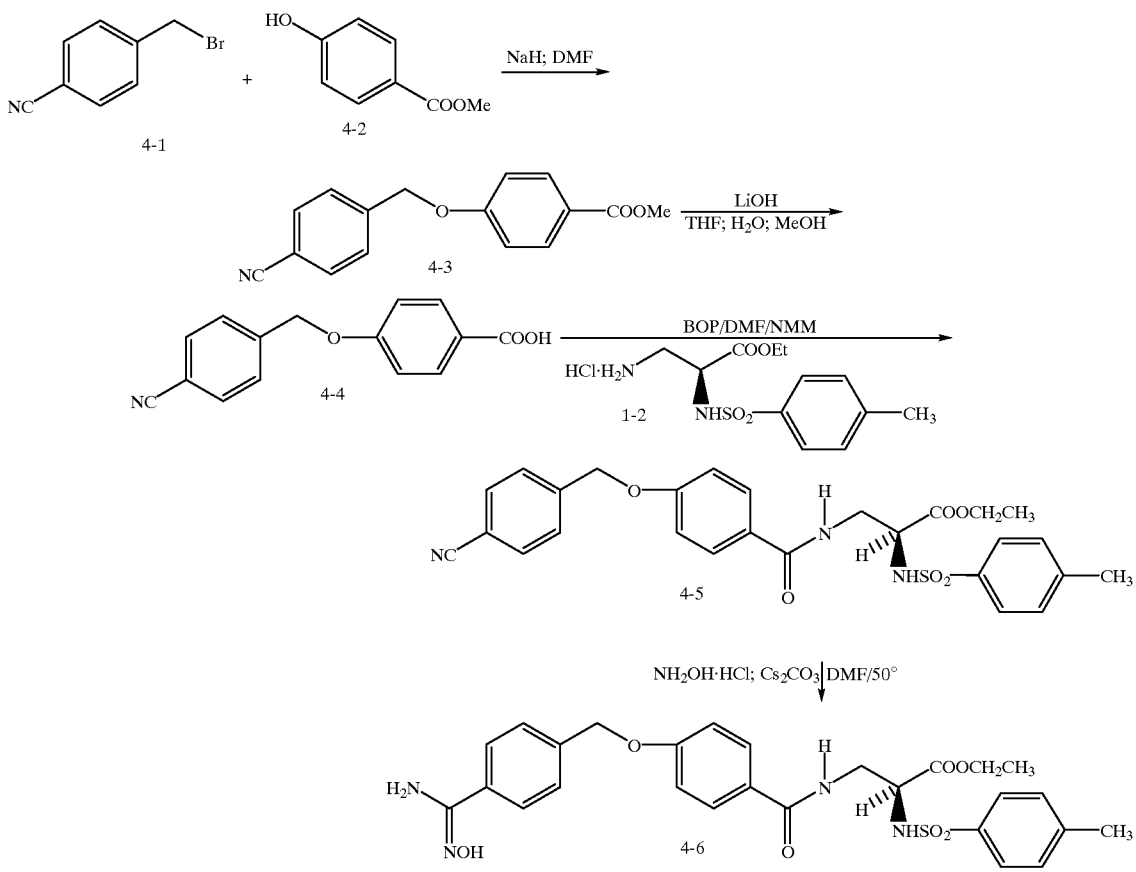

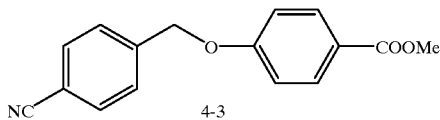
4-3

4-(4-Cyanobenzyloxy)benzoic acid methyl ester 4-3

4-Methyl hydroxy benzoate(3.9 g; 5.5 mmol) was dissolved in DMF. $Cs_2CO_3$ (4.2 g; 12.8 mmol) was added and the slurry was stirred vigorously for 0.5 hr. Alpha-bromo-p-tolunitrile (5.0 g; 25.5 mmol) was added and the reaction was stirred for 16 hrs. The reaction mixture is diluted with EtOAc and washed with $H_2O$ (2×) and brine. The organic layer was dried ($MgSO_4$), filtered and concentrated to yield 4-3 as a white solid.

$^1$H NMR (400 MHz; CDCl$_3$) d 8.02 (d, 2H); 7.70 (d, 2H); 7.56 (d, 2H); 5.18 (s, 2H); 3.89 (s, 3H).

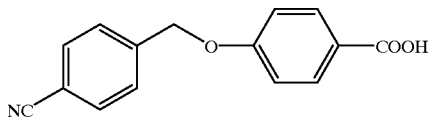
4-4

4-(4-Cyanobenzyloxy)benzoic acid 4-4

4-3 (1.4 g; 5.2 mmol) was slurried in THF/H$_2$O/MeOH. LiOH (1.09 g; 26 mmol) was added and the reaction was stirred for 20 hr. The resulting homogeneous reaction mixture was treated with EtOAc and 10% KHSO$_4$. The layers were separated, and the organic layer was washed with H$_2$O and brine, dried (MgSO$_4$) filtered and concentrated to yield 4-4 as a white solid.

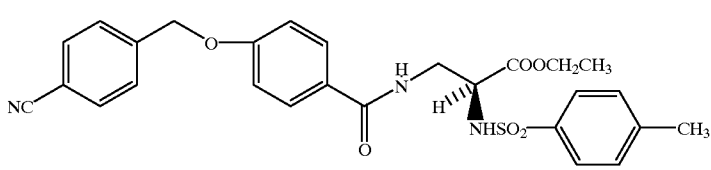
4-5

(R)-3-[4-(4-Cyanobenzyloxy)benzoylamino]-2-(toluene-4-sulfonylamino)propionic acid ethyl ester 4-5

4-4 (500 mg; 1.98 mmol) and 1-2 (630 mg; 1.98 mmol) are dissolved in DMF. BOP (875 mg; 1.98 mmol) and NMM (0.44 mL; 3.96 mmol) are added and the reaction is stirred for 1.5 hrs. The reaction mixture is diluted with EtOAc, and washed with H$_2$O (2×), 10% KHSO$_4$, sat NaHCO$_3$ and brine. The organic layer was dried, (MgSO$_4$), filtered, and concentrated to yield 4-5 as a white solid.

1H NMR (400 MHz; CDCl$_3$) d 7.79–7.69 (m, 6H); 7.56–7.54 (d, 2H); 7.29–7.27 (d, 2H); 7.00 (d, 2H); 6.67–6.65 (t, 1H); 5.63–5.61 (d, 1H); 5.18 (s, 2H); 4.09–3.99 (m, 4H); 3.64–3.60 (m, 1H); 2.41 (s, 3H); 1.17–1.15 (t, 3H).

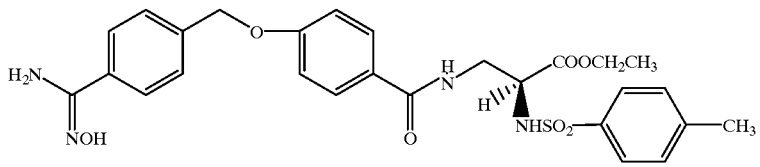
4-6

(R)-3-{4-[4-(N-hydroxycarbamimidoyl)benzyloxy]benzoylamino}-2-(toluene-4-sulfonylamino)propionic acid ethyl ester 4-6

4-6 was prepared substantially the same as for example 1-5.

$^1$H NMR (400 MHz; DMSO-d$_6$) d 10.90 (bs, 1H); 8.33 (t, 1H); 8.27–8.25 (d, 1H); 7.70–7.69 (m, 4H); 7.62–7.61 (m, 4H); 7.29–7.27 (d, 2H); 7.05–7.07 (d, 2H); 5.27 (s, 2H); 4.05 (m, 1H); 3.49 (m, 1H); 3.45 (m, 1H); 2.3 (s, 3H); 0.96–0.93 (t, 3H).

EXAMPLE 5
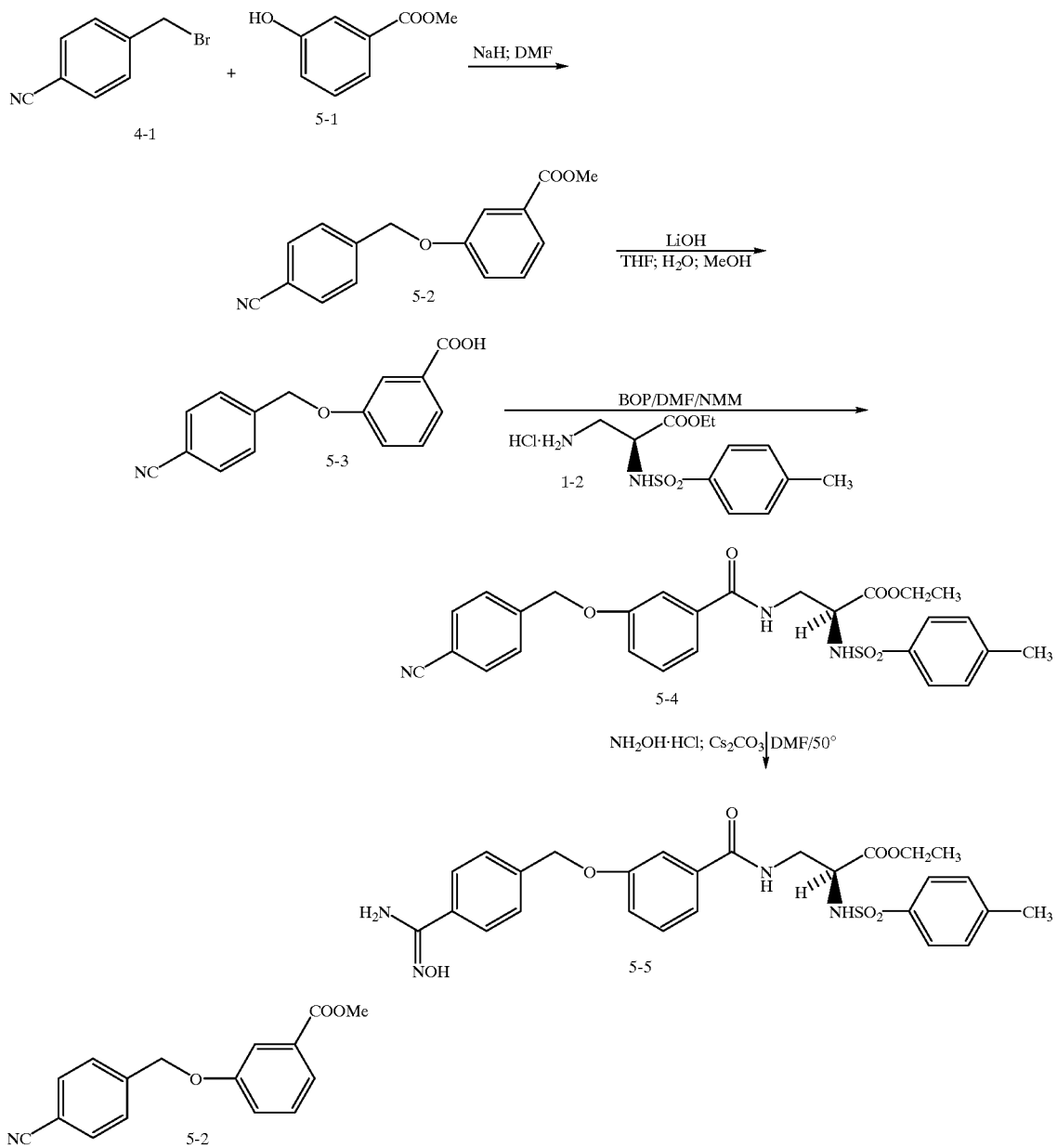
4-(3-Cyanobenzyloxy)benzoic acid methyl ester 5-2
5-2 was prepared in a manner substantially similiar as for example 4-3
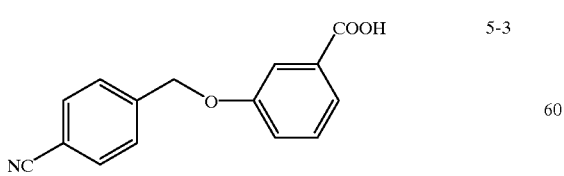
4-(3-Cyanobenzyloxy)benzoic acid 5-3
5-3 was prepared in a manner substantially similiar as for example 4-4

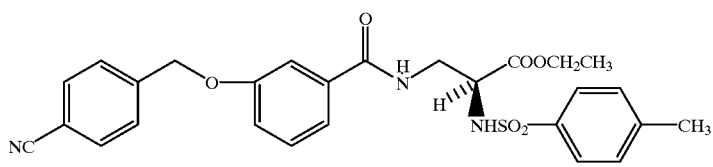

(R)-3-[3-(4-Cyanobenzyloxy)benzoylamino]-2-(toluene-4-sulfonylamino)propionic acid ethyl ester
5-4

5-4 was prepared in a manner substantially similiar as for example 4-5.

$^1$H NMR (400 MHz; CDCl$_3$) d 7.73–7.68 (m, 4H); 7.58–7.56 (d, 2H); 7.45 (s, 1H); 7.38–7.37 (d, 2H); 7.30–7.28 (d, 2H); 7.10 (m, 1H); 6.75 (t, 1H); 5.61 (d, 1H); 5.20 (s, 2H); 4.09–4.06 (m, 4H); 3.60 (m, 1H); 2.41 (s, 3H); 1.18–1.14 (t, 3H).

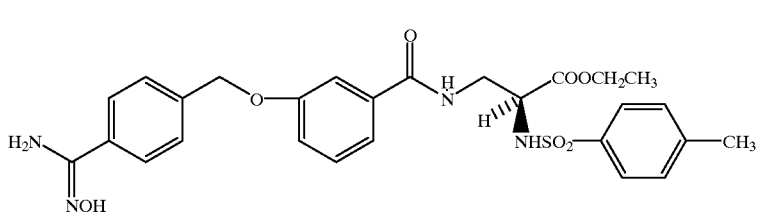

(R)-3-{3-[4-(N-hydroxycarbamimidoyl)benzyloxy]benzoylamino}-2-(toluene-4-sulfony lamino)propionic acid ethyl ester 5-5

5-5 was prepared in a manner substantially similiar as for example 1-5.

1H NMR (400 MHz; DMSO-d$_6$) d 10.95 (vbs, 1H); 8.49 (t, 1H); 8.30 (d, 1H); 7.73–7.71 (d, 1H); 7.64–7.62 (m, 2H); 7.39–7.35 (m, 3H); 7.18 (d, 1H); 5.25 (s, 2H); 4.07–4.05 (m, 1H); 3.83–3.81 (q, 2H); 3.45 (m, 1H); 3.25 (m, 1H); 2.30 (s, 3H); 0.97–0.95 (t, 3H).

EXAMPLE 6

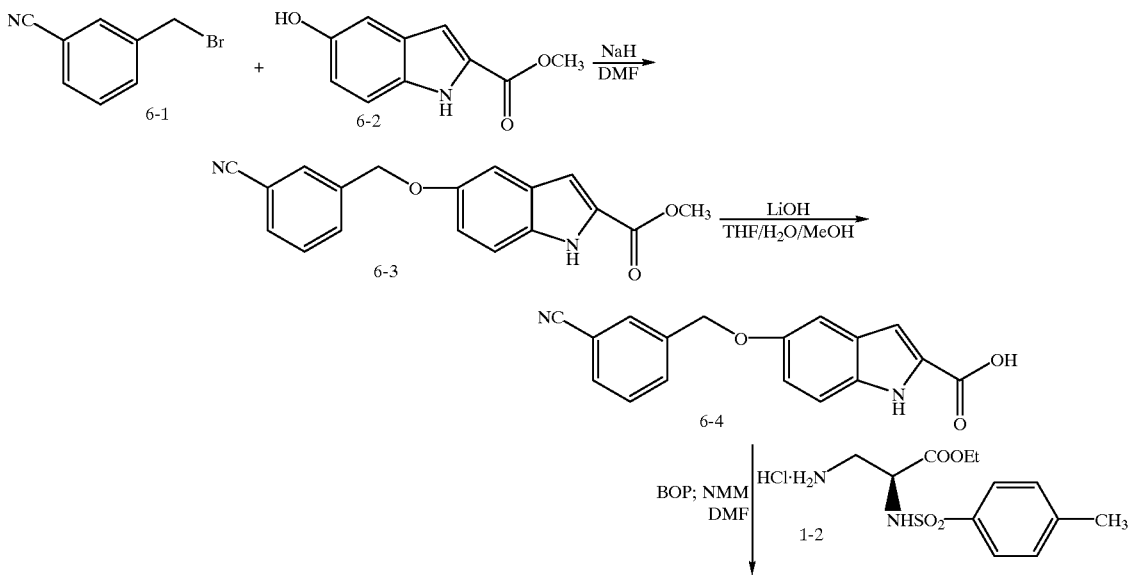

-continued

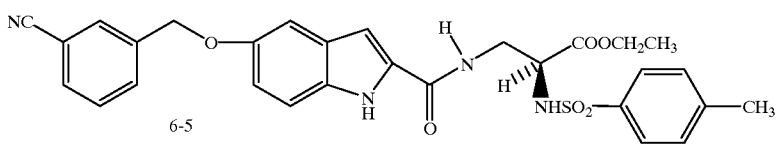
6-5

Cs₂CO₃; NH₂OH·HCl
DMF; 50°

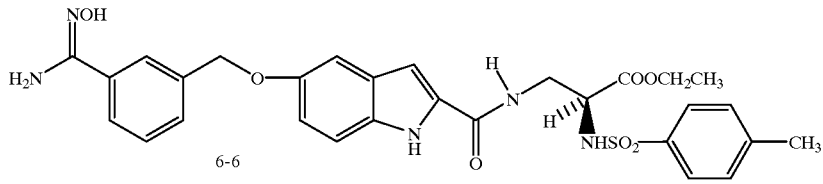
6-6

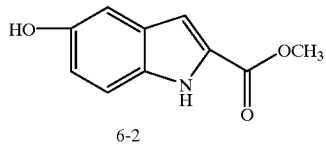
6-2

5-Hydroxy-1H-indole-2-carboxylic acid methyl ester 6-2

5-Hydroxy-2-indolecarboxylic acid (2.3 g; 13 mmol) was dissolved in MeOH and cooled to 0°. HCl (g) was bubbled through until the solution was saturated. The reaction mixture was stirred for 2 days allowing the cooling bath to evaporate. The reaction mixture was concentrated to yield 6-2 as a tan solid.

$^1$H NMR (400 MHz; CDCl₃) d 8.82 (bs, 1H); 7.27–7.30 (m, 1H); 7.10–7.07 (dd, 2H); 6.95 (d, 1H); 4.69 (s, 1H); 3.95 (s, 3H).

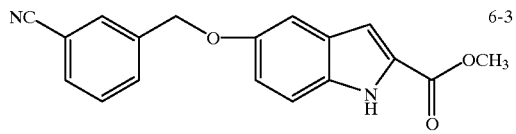
6-3

5-(3-Cyanobenzyloxy)-1H-indole-2-carboxylic acid methyl ester 6-3

6-2 was dissolved in DMF. NaH (9.5 mmol; 380 mg of a 60% dispersion on mineral oil) was added and the reaction mixture was stirred for 15 minutes. Alpha-bromo-meta-tolunitrile (9.5 mmol; 1.8 g) was added and the reaction mixture was stirred for 18 hours. The DMF was removed in vacuo to yield a brown viscous oil. Flash chromatography (10% EtOAc/Hexanes) yielded 6-3 as a white solid.

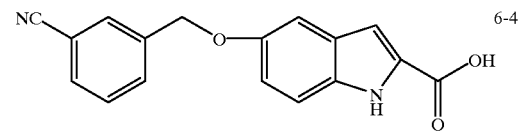
6-4

5-(3-Cyanobenzyloxy)-1H-indole-2-carboxylic acid 6-4

6-3 (2.0 g; 6.5 mmol) was slurried in THF/H₂O/MeOH (10 mL/10mL/10 mL), LiOH (19.5 mmol; 820 mg) was added and the reacion mixture was stirred for 18 hours. The homogeneous reaction mixture was neutralized to pH=8 and concentrated to yield 6-4 as a brown oil which will be used as is in the next step.

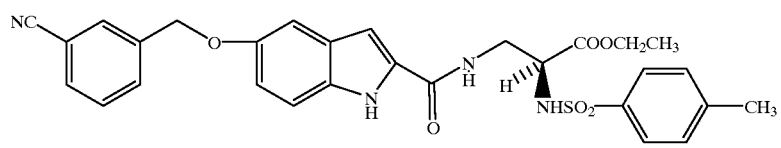
6-5

(R) 3-({5-[3-Cyanobenzyloxy)-1H-indole-2-carbonyl]amino}-2-(toluene-4-sulfonylamino) propionic acid ethyl ester 6-5

6-4 (1.6 g; 5.4 mmol) and 1-2 (5.4 mmol; 1.7 g) were dissolved in DMF. BOP (5.4 mmol; 2.4 g) and NMM (10.8 mmol; 1.18 mL) were added and the reaction mixture was stirred for 2 days. The reaction mixture was diluted with EtOAc and H₂O. The layers were separated and the organic layer was washed with H₂O and brine, dried (MgSO₄), filtered and concentrated to yield a tan oil. Flash chromatography (50% EtOAc/hexanes) yielded 6-5 as a white solid.

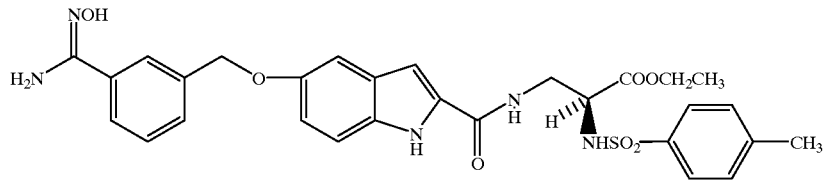
(R) 3-({5-[3-(N-hydroxycarbamimidoyl)benzyloxy]-1H-indole-2-carbonyl}-amino)-2-(toluene-4-sulfonylamino)propionic acid ethyl ester 6-6
6-6 was prepared in a manner substantially similiar to example 1-5.
1H NMR (400 MHz; DMSO-$d_6$) d 11.40 (s, 1H); 8.30 (t, 1H); 8.21 (d, 1H); 7.80 (s, 1H); 7.82–7.62 (m, 5H); 7.26 (d, 1H); 7.23 (d, 2H); 7.20 (s, 1H); 6.95 (d, 1H); 6.93 (s, 1H); 5.15 (s, 2H); 4.05 (m, 1H); 3.81 (m, 2H); 2.24 (s, 3H); 0.95 (t, 3H).
EXAMPLE 7
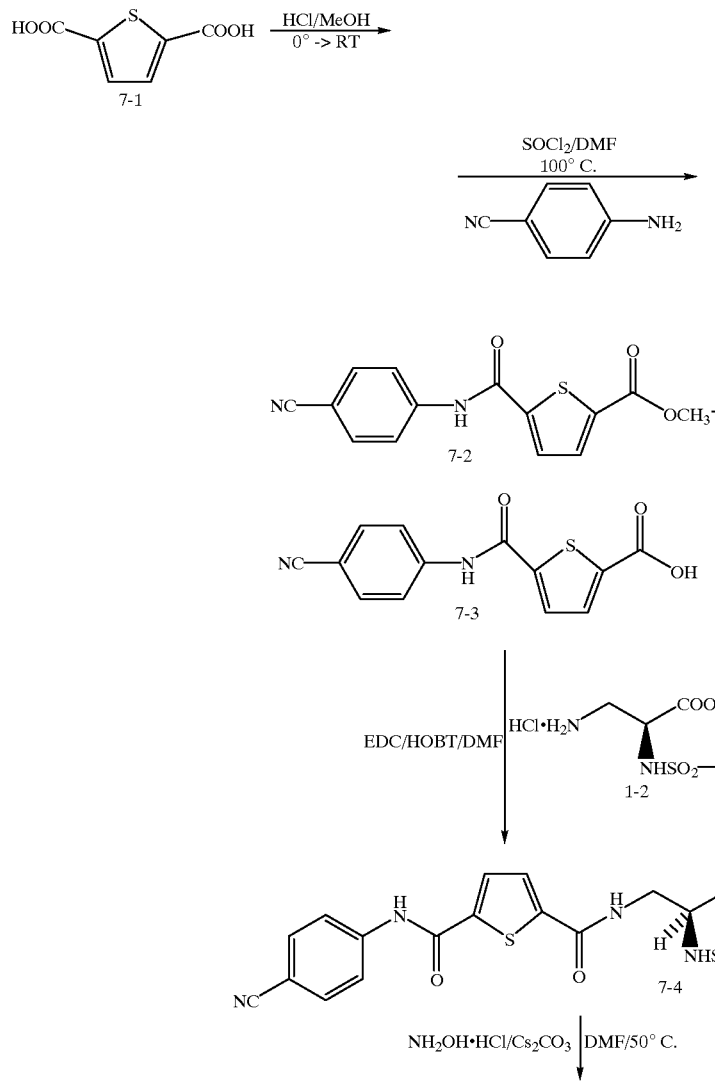

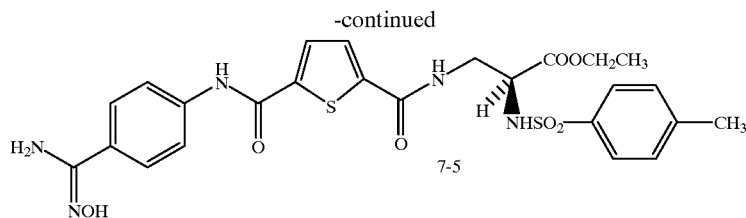

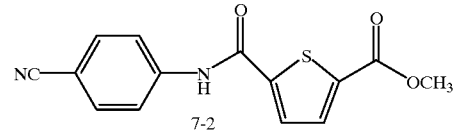

5-(4-Cyanophenylcarbamoyl)thiophene-2-carboxylic acid methyl ester 7-2

A solution of 2,5-thiophenedicarboxylic acid (7-1, 2.52 g, 14.6 mmol) in 100 mL $CH_3OH$ was cooled to 0° C. and treated with HCl (g) for 5 min. The mixture was stirred for 4 h at rt, at which time HPLC analysis indicated an approximately 1:1 mixture of mono- and di-esters. The precipitated solids were filtered off, and the filtrate concentrated and azeotroped with $CH_2Cl_2$ to afford a white solid consisting of 60% mono-acid/mono-ester, 33% diester, and 6% residual starting material. A portion of this mixture (0.73 g, ~4 mmol) suspended in 20 mL dichloroethane was treated with thionyl chloride (2.9 mL, 40 mmol) and 1 drop DMF and heated at 100° C. for 30 min. After cooling to rt, the mixture was concentrated and azeotroped with dichloroethane and toluene. The residue was transferred with 10 mL $CHCl_3$ to a jacketed addition funnel cooled to 0° C., and added dropwise to a solution of 4-aminobenzonitrile (0.47 g, 4.0 mmol) and pyridine (0.9 mL, 10 mmol) in 20 mL $CHCl_3$ at 0° C. The resulting mixture was stirred for 1 h at rt then concentrated in vacuo, and the residue purified by chromatography on $SiO_2$ eluting with a gradient of 2% to 5% to 10% $Et_2O$ in $CHCl_3$ to afford 7-2 as a white solid. $R_f$ (5% $Et_2O/CHCl_3$): 0.11. NMR (400 MHz, d-6 DMSO-$d_6$): d 8.06 (d, J=4 Hz, 1H), 7.93 (d, J=8.6 Hz, 2H), 7.88 (d, J=4 Hz, 1H), 7.82 (d, J=8.6 Hz, 2H), 3.86 (s, 3H).

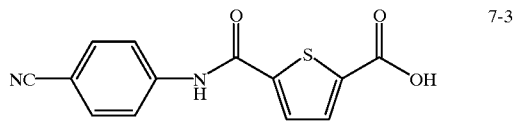

5-(4-Cyano-phenylcarbamoyl)thiophene-2-carboxylic acid 7-3

7-2 (350 mg, 1.22 mmol) was slurried in $THF/H_2O/MeOH$. LiOH (3.66 mmol; 154 mg.) was added and the reaction mixture was stirred at room temperature for 16 hours. The resulting homogeneous reaction mixture was then heated at 50° for four hours. After cooling, the reaction mixture was diltuted with EtOAc and 10% $KHSO_4$. The organic layer was washed with H2O and brine, dried ($MgSO_4$) filtered and concentrated to yield 7-3 as a white solid.

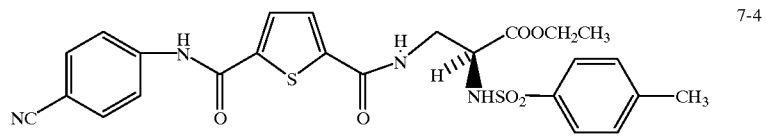

(R)-3-{[5-(4-Cyanophenylcarbamoyl)thiophene-2-carbonyl]-amino}-2-(toluene-4-sulfonylamino) propionic acid ethyl ester 7-4

7-3 (350 mg; 1.29 mmol) and 1-2 (1.29 mmol; 414 mg.) were dissolved in DMF. HOBT (1.29 mmoll; 197 mg) and EDC (1.29 mmol; 247 mg) were added and the reaction mixture was stirred for 2 days. The reaction mixture was then diluted with EtOAc and $H_2O$ The layers were separated, and the organic layer was washed with H2O, 10% $KHSO_4$, sat. $NaHCO_3$, and brine. The organic layer was then dried ($MgSO_4$), filtered and concentrated to yield a tan oil. Flash chromatography (60% EtOAc/Hexanes) yielded 7-4 as a white solid.

$^1H$ NMR (400 MHz, $CDCl_3$) d 8.14 (s, 1H); 7.8 (d, 2H); 7.73 (d, 2H); 7.68 (d, 2H); 7.64 (d, 1H); 7.60 (d, 1H); 7.32 (d, 2H); 7.01 (t, 1H); 6.70 (d, 1H); 4.09–3.99 (m, 4H); 3.55 (m, 1H); 2.42 (s, 3H); 1.13 (t, 3H).

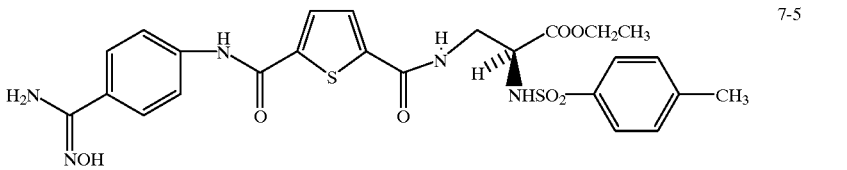

7-5

(R)-3-({5-[4-(N-hydroxycarbamimidoyl)
phenylcarbamoyl]thiophene-2-carbonyl}amino)-2-
(toluene-4-sulfonylamino)propionic acid ethyl ester
7-5

7-5 was prepared in a manner substantially similiar to example 1-5.

$^1$H NMR (400 MHz, DMSO-$d_6$) d 10.9 (bs, 1H); 10.63 (s, 1H); 8.75 (t, 1H); 8.31 (d, 1H); 8.0 (m, 1H); 7.9 (d, 1H); 7.69–7.61 (m, 5H); 7.23 (d, 2H); 4.03 (m, 1H); 3.85 (q, 2H); 3.5 (m, 1H); 3.35 (m, 1H); 2.48 (s, 3H); 0.990 (t, 3H).

EXAMPLE 8

Tablet Preparation

Tablets containing 25.0, 50.0, and 100.0 mg., respectively, of the compound (R)-3-({5-[4-(N-hydroxycarbamimidoyl) benzyl]-4-oxo-5,6,7,8-tetrahydro-4H-1,5,8a-triazaazulene-2-carbonyl}amino)-2-(toluene-4-sulfonylamino)propionic acid ethyl ester (Compound,A) are prepared as illustrated below:

Table for Doses Containing from 25–100 mg of Compound A

|  | Amount-mg | | |
| --- | --- | --- | --- |
| Compound A | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 9

Intravenous formulations

An intravenous dosage form of the above-indicated active compound is prepared as follows:

| Compound A | 0.5–10.0 mg |
| --- | --- |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

What is claimed is:

1. A compound having the formula

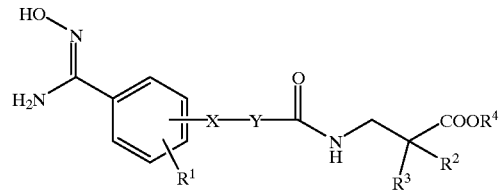

or a pharmaceutically acceptable salt, wherein
X is
$(CH_2)_q$,
$(CH_2)_mO(CH_2)_p$,
$(CH_2)_mNR^{11}(CH_2)_p$,
$(CH_2)_mC(O)NR^{11}(CH_2)_p$,
$(CH_2)_mNR^{11}C(O)(CH_2)_p$,
$(CH_2)_mC(O)(CH_2)_p$,
$(CH_2)_mC(S)(CH_2)_p$,
$(CH_2)_mSO_2(CH_2)_p$,
$(CH_2)_mS(CH_2)_p$,
$(CH_2)_mSO(CH_2)_p$,
$(CH_2)_mSO_2NR^{11}(CH_2)_p$,
$(CH_2)_mC=C(CH_2)_p$, or
$(CH_2)_mCH(OH)(CH_2)_p$,
where m and p are integers independently chosen from 0–6, q is an integer chosen from 1–6, and $R^{11}$ is selected from the group consisting of
hydrogen,
hydroxyl,
$C_{1-10}$ allyl,
$C_{3-8}$ cycloalkyl,
aryl,
aryl $C_{1-8}$ alkyl-,
amino,
amino $C_{1-8}$ alkyl-,
$C_{1-3}$ acylamino-,
$C_{1-3}$ acylamino $C_{1-8}$ alkyl-,
$C_{1-6}$ alkylamino-,
$C_{1-6}$ alkylamino-, $C_{1-8}$ alkyl-,
$C_{1-6}$ dialkylamino-,
$C_{1-6}$ dialkylamino $C_{1-8}$ alkyl-,
$C_{1-4}$ alkoxy,
$C_{1-4}$ alkoxy $C_{1-6}$ alkyl-,
carboxy,
carboxy $C_{1-6}$ alkyl-,
$C_{1-3}$ alkoxycarbonyl-,
$C_{1-3}$ alkoxycarbonyl $C_{1-6}$ alkyl-,
carboxyoxy-,
carboxy $C_{1-6}$ alkyloxy-,
hydroxy $C_{1-6}$ alkyl-,
$C_{1-8}$ alkylcarbonyloxy $C_{1-4}$ alkyloxycarbonyl-, and aryl C$_{1-8}$ alkylcarbonyloxy C$_{1-4}$ alkyloxycarbonyl-;
Y is

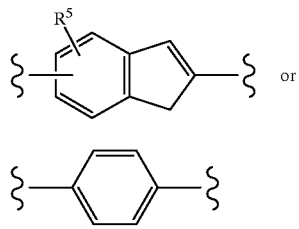 or

R$^1$ is
hydrogen
C$_{1-6}$ alkyl-,
carboxy,
carboxy C$_{1-6}$ alkyl,
C$_{1-6}$ alkylcarboxy-,
C$_{1-6}$ alkylcarboxy C$_{1-6}$ alkyl-,
oxo,
C$_{1-6}$ alkyloxy-,
oxo C$_{1-6}$ alkyl-,
C$_{1-6}$ alkyloxy C$_{1-6}$ alkyl-,
hydroxy,
hydroxy C$_{1-6}$ alkyl-,
aryl,
aryl C$_{1-6}$ alkyl-, or
halogen;
R$^2$ and R$^3$ are independently selected from the group consisting of
hydrogen,
fluoro,
hydroxy C$_{1-6}$ alkyl-,
carboxy,
carboxy C$_{1-6}$ alkyl-,
hydroxyl,
C$_{1-6}$ alkyloxy-,
aryl C$_{1-6}$alkyloxy-,
C$_{3-8}$ cycloalkyl-,
C$_{1-8}$ alkyl-,
aryl,
aryl C$_{1-6}$ alkyl-,
C$_{1-6}$ alkylcarbonyloxy-,
amino,
C$_{1-6}$ alkylamino-,
amino C$_{1-6}$ alkyl-,
C$_{1-6}$ alkylamino-, C$_{1-6}$ alkyl-,
arylamino-,
aryl C$_{1-6}$ alkylamino-,
arylamino C$_{1-6}$ alkyl-,
aryl C$_{1-6}$ alkylamino-, C$_{1-6}$ alkyl-,
amino C$_{1-6}$ alkyl-,
C$_{1-6}$ dialkylamino-,
C$_{1-6}$ dialkylamino C$_{1-6}$alkyl-,
aminocarbonyloxy-,
aminocarbonyloxy C$_{1-6}$ alkyl-,
C$_{1-6}$ alkylaminocarbonyloxy-,
C$_{1-6}$ alkylaminocarbonyloxy C$_{1-6}$ alkyl-,
aryl aminocarbonyloxy-,
aryl aminocarbonyloxy C$_{1-6}$ alkyl-,
aryl C$_{1-6}$ alkylaminocarbonyloxy-,
aryl C$_{1-6}$ alkylaminocarbonyloxy C$_{1-6}$ alkyl-,
C$_{1-8}$ alkylsulfonylamino-,
C$_{1-8}$ alkylsulfonylamino C$_{1-6}$ alkyl-,
aryl sulfonylamino-,
aryl sulfonylamino C$_{1-6}$ alkyl-,
aryl C$_{1-6}$ alkylsulfonylamino-,
aryl C$_{1-6}$ alkylsulfonylamino C$_{1-6}$ alkyl-,
C$_{1-8}$ alkyloxycarbonylamino-,
C$_{1-8}$ alkyloxycarbonylamino C$_{1-8}$ alkyl-,
aryloxycarbonylamino-,
aryloxycarbonylamino C$_{1-8}$ alkyl-,
aryl C$_{1-8}$ alkyloxycarbonylamino-,
aryl C$_{1-8}$ alkyloxycarbonylamino C$_{1-8}$ alkyl-,
C$_{1-8}$ alkylcarbonylamino-,
C$_{1-8}$ alkylcarbonylamino C$_{1-6}$ alkyl-,
arylcarbonylamino-,
arylcarbonylamino C$_{1-6}$ alkyl-,
aryl C$_{1-8}$ alkylcarbonylamino-,
aryl C$_{1-8}$ alkylcarbonylamino C$_{1-6}$ alkyl-,
aminocarbonylamino-,
aminocarbonylamino C$_{1-6}$ alkyl-,
C$_{1-8}$ alkylamino-,carbonylamino-,
C$_{1-8}$ alkylaminocarbonylamino C$_{1-6}$ alkyl-,
arylaminocarbonylamino-,
arylaminocarbonylamino C$_{1-6}$ alkyl-,
aryl C$_{1-8}$ alkylamino carbonylamino-,
aryl C$_{1-8}$ alkylamino, carbonylamino C$_{1-6}$ alkyl-,
aminosulfonylamino-,
aminosulfonylamino C$_{1-6}$ alkyl-,
C$_{1-8}$ alkylaminosulfonylamino-,
C$_{1-8}$ alkylaminosulfonylamino C$_{1-6}$ alkyl-,
arylaminosulfonylamino-,
arylaminosulfonylamino C$_{1-6}$ alkyl-,
aryl C$_{1-8}$ alkylaminosulfonylamino-,
aryl C$_{1-8}$ alkylaminosulfonylamino C$_{1-6}$ alkyl-,
C$_{1-6}$ alkylsulfonyl-,
C$_{1-6}$ alkylsulfonyl C$_{1-6}$ alkyl-,
aryl C$_{1-6}$ alkylsulfonyl-,
aryl C$_{1-6}$ alkylsulfonyl C$_{1-6}$ alkyl-,
C$_{1-6}$ alkylcarbonyl-,
C$_{1-6}$ alkylcarbonyl C$_{1-6}$ alkyl-,
aryl C$_{1-6}$ alkylcarbonyl-,
aryl C$_{1-6}$ alkylcarbonyl C$_{1-6}$ alkyl-,
aminocarbonyl-,
aminocarbonyl C$_{1-8}$ alkyl-,
C$_{1-8}$ alkylaminocarbonyl-,
C$_{1-8}$ alkylaminocarbonyl C$_{1-8}$ alkyl-,
arylaminocarbonyl-,
arylaminocarbonyl C$_{1-8}$ alkyl-,
aryl C$_{1-8}$ alkylaminocarbonyl-,
aryl C$_{1-8}$ alkylaminocarbonyl C$_{1-8}$ alkyl-,
aminosulfonyl-,
aminosulfonyl C$_{1-8}$ alkyl-,
C$_{1-8}$ alkylaminosulfonyl-,
C$_{1-8}$ alkylaminosulfonyl C$_{1-8}$ alkyl-,
arylaminosulfonyl-,
arylaminosulfonyl C$_{1-8}$ alkyl-,
aryl C$_{1-8}$ alkylaminosulfonyl-,
aryl C$_{1-8}$ alkylaminosulfonyl C$_{1-8}$ alkyl-,
C$_{3-8}$ cycloalkylsulfonylamino-,
C$_{1-8}$ alkyloxyarylsulfonylamino-, thiophenylsulfonylamino-, and
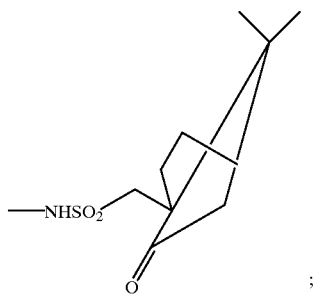
and
R⁴ is
- hydrogen,
- $C_{1-8}$ alkyl,
- aryl,
- aryl $C_{1-6}$ alkyl-,
- $C_{1-8}$ alkylcarbonyloxy $C_{1-4}$ alkyl-, or
- aryl $C_{1-8}$ alkylcarbonyloxy $C_{1-4}$ alkyl-.
2. A compound of claim 1 having the formula or a pharmaceutically acceptable salt, wherein
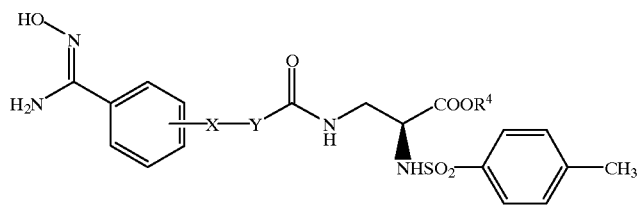
wherein
X is —CH₂—, —O—, —CH₂—O—, or —NH—C(O)—;
R⁴ is —CH₂CH₃ or —C(CH₃)₃.
3. A compound of claim 1 selected from the group consisting of
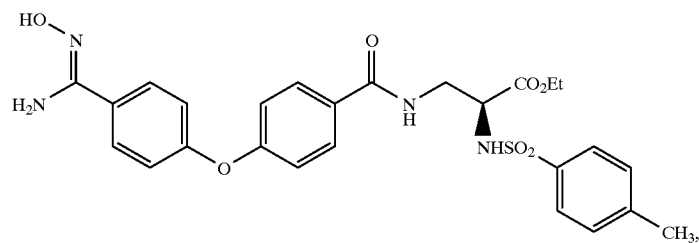
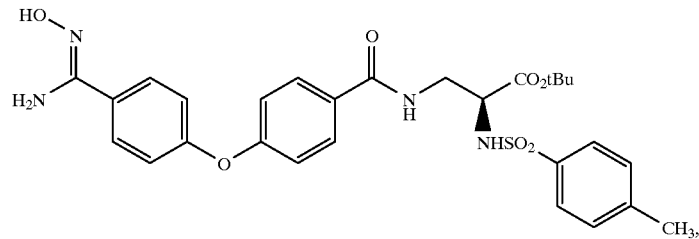
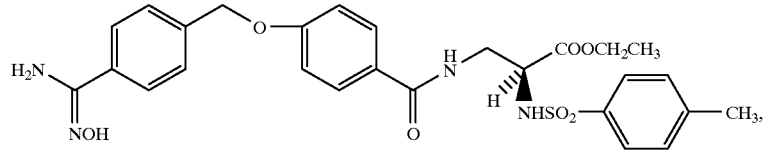

-continued

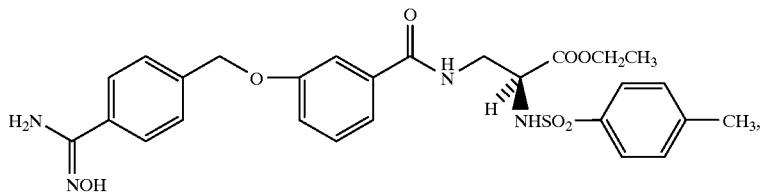

or a pharmaceutically acceptable salt thereof.

4. A compound of claim 1 for use in inhibiting the binding of fibrinogen to blood platelets, inhibiting the aggregation of blood platelets, treating thrombus formation or embolus formation, or preventing thrombus or embolus formation in a mammal.

5. A composition comprising a compound of claim 1 and a pharmaceutically acceptable carrier.

6. A method for inhibiting the binding of fibrinogen to blood platelets in a mammal, comprising treating the mammal with a composition of claim 5.

7. A method for inhibiting the aggregation of blood platelets in a mammal, by blocking fibrinogen from acting at its receptor site, comprising treating the mammal with a composition of claim 5.

8. A composition for inhibiting the aggregation of blood platelets in a mammal, comprising an efficacious amount of a compound of claim 1 in combination with one or more agents selected from a thrombolytic agent, an anticoagulant agent, and an antiplatelet agent and a pharmaceutically acceptable carrier.

9. A method for inhibiting the aggregation of blood platelets in a mammal, by blocking fibrinogen from acting at its receptor site, comprising treating the mammal with a composition of claim 8.

10. A method for inhibiting the binding of fibrinogen to blood platelets in a mammal, by blocking fibrinogen from acting at its receptor site, comprising treating the mammal with a composition of claim 8.

11. A method for inhibiting osteoclast mediated bone resorption, comprising treating the mammal with a composition of claim 5.

12. A method for inhibiting angiogenesis in a mammal comprising treating the mammal with a composition of claim 5.

13. A method for inhibiting tumor growth in a mammal comprising treating the mammal with a composition of claim 5.

* * * * *